US007626005B2

(12) United States Patent
Auclair et al.

(10) Patent No.: US 7,626,005 B2
(45) Date of Patent: Dec. 1, 2009

(54) INHIBITORS OF AMINOGLYCOSIDE 6'-N-ACETYLTRANSFERASES, COMPOSITIONS AND USES THEREOF

(75) Inventors: Karine Auclair, Laval (CA); Feng Gao, Montréal (CA); Xuxu Yan, Montréal (CA)

(73) Assignee: McGill University, Montreal (CA)

( * ) Notice: Subject to any disclaimer, the term of this patent is extended or adjusted under 35 U.S.C. 154(b) by 119 days.

(21) Appl. No.: 11/359,274

(22) Filed: Feb. 21, 2006

(65) Prior Publication Data

US 2006/0211634 A1 Sep. 21, 2006

Related U.S. Application Data

(60) Provisional application No. 60/653,979, filed on Feb. 18, 2005.

(51) Int. Cl.
*C07H 15/20* (2006.01)
*C07G 11/00* (2006.01)
*A01N 43/04* (2006.01)
*A61K 31/70* (2006.01)

(52) U.S. Cl. .................. 536/16.6; 536/16.8; 514/62

(58) Field of Classification Search ............... None
See application file for complete search history.

(56) References Cited

OTHER PUBLICATIONS

Sugimoto, T., Fujii, T., Hatanaka, Y., Yamamura, S., and Ueda, M. Syntheses of novel photoaffinity probes for bioorganic studies on nyctinasty of leguminous plants. (2002) Tetrahedron Letters, v. 43, p. 6529-6532.*
Gao, F. et al. (2006) Synthesis and Structure-Activity Relationships of Truncated Bisubstrate Inhibitors of Aminoglycoside 6'-N-Acetyltransferases. Journal of Medicinal Chemistry, vol. 49, p. 5273-5281.*
Gao, F., Yan, X., Baettig, O.M., Berghuis, A.M., Auclair, K. (2005) Regio- and Chemoselective 6'-N-Derivatization of Aminoglycosides: Bisubstrate Inhibitors as Probes to Study Aminoglycoside 6-N-Acetyltransferases. Angewandte Chemie International Edition, vol. 44, p. 6859-6862.*
The Merck Manual - Second Home Edition, chapter 192, p. 1-5. [retrieved online Sep. 6, 2008].*
Agnelli et al., "Dimeric Aminoglycosides as Antibiotics," *Agnew. Chem. Int. Ed.*, 43:1562-1566, 2004.
Alper et al., "Metal Catalyzed Diazo Transfer for the Synthesis of Azides From Amines," *Tet. Lett.*, 37:6029-6032, 1996.
Arya et al., "Aminoglycoside—Nucleic Acid Interactions: Remarkable Stabilization of DNA and RNA Triple Helices by Neomycin," *J. Am. Chem. Soc.*, 123:5385-5395, 2001.
Arya et al., "Aminoglycoside (neomycin) preference is for A-form nucleic acids, not just RNA: results from a competition dialysis study," *J. Am. Chem. Soc.*, 125:10148-10149, 2003.
Arya et al., "From triplex to B-form duplex stabilization: reversal of target selectivity by aminoglycoside dimers," *Bioorg. Med. Chem. Lett.*, 14:4643-4646, 2004.

Arya et al., "Neomycin-induced hybrid triplex formation," *J. Am. Chem. Soc.*, 123:11093-11094, 2001.
Azucena and Mobashery, "Aminoglycoside-modifying enzymes: mechanisms of catalytic processes and inhibition," *Drug Resistance Updates*, 4:106-117, 2001.
Boehr et al., "Domain-Domain Interactions in the Aminoglycosides Antibiotic Resistance Enzyme AAC(6')- APH(2")," *Biochemistry*, 43:9846-9855, 2004.
Boto and Coxon, "Nitrogen-15 Nulcear Magnetic Resonance Spectroscopy of Neomycin B and Related Aminoglycosides," *J. Am. Chem. Soc.*, 105:1021-1028, 1983.
Burk et al., "X-ray structure of the AAC(6')-Ii antibiotic resistance enzyme at 1.8 A resolution; examination of oligomeric arrangements in GNAT superfamily members," *Prot. Sci.*, 12:426-437, 2003.
Chou et al., "Regioselective Glycosylation of Neamine Core: A Facile Entry to Kanamycin B Related Analogues," *Org. Lett.*, 6:585-588, 2004.
Coates et al., "The Future Challenges Facing the Development of New Antimicrobial Drugs," *Nat. Rev.*, 1:895-910, 2002.
Culebras and Martinez, "Aminoglycoside resistance mediated by the bifunctional enzyme 6'-N-Aminoglycoside Acetyltransferase-2"-O-Aminoglycoside Phosphotransferase," *Front. Biosci.*, 4:D1-D8, 1999.
Ding et al., "Design and Synthesis of Paromomycin-Related Hetrocycle-Substituted Aminoglycoside Mimetics Based on a Mass Spectrometry RNA-Binding Assay," *Angew. Chem. Int. Ed.*, 42:3409-3412, 2003.
Ding et al., "Efficient synthesis of neomycin B related aminoglycosides," *Tet. Lett.*, 41:4049-4052, 2000.
Draker and Wright, "Molecular Mechanism of the Enterococcal Aminoglycoside 6'-N-Acetyltransferase: Role of GNAT-Conserved Residues in the Chemistry of Antibiotic Inactivation," *Biochemistry*, 43:446-454, 2004.
Draker et al., "Kinetic Mechanism of the GCN5-Related Chromosomal Aminoglycoside Acetyltransferase AAC(6')-Ii from *Enterococcus faecium*: evidence of Dimer Subunit Cooperativity," *Biochemistry*, 42:6565-6574, 2003.
Fourmy et al., "Binding of neomycin-class aminoglycoside antibiotics to the A-site of 16 S rRna," *J. Mol. Biol.*, 277:347-362, 1998.
Fourmy et al., "Structure of the A Site of *Escherichia coli* 16S Ribosomal RNA Complexed with and Aminoglycoside Antibiotic," *Science*, 274:1367-1375, 1997.
Gallego and Varani, "Targeting RNA with small-molecule drugs: therapeutic promise and chemical challenges," *Acc. Chem. Res.*, 34:836-843, 2001.
Georgiadis and Constantinou-Kokotou, "Synthesis of Amino Acid Derivatives of Neamine and 2-Deoxystreptamine to be use as Mutasynthons," *J. Carb. Chem.*, 10:739-748, 1991.

(Continued)

*Primary Examiner*—Shaojia Anna Jiang
*Assistant Examiner*—Scarlett Goon
(74) *Attorney, Agent, or Firm*—Fulbright & Jaworski

(57) ABSTRACT

The present invention relates to novel inhibitors of aminoglycoside 6'-N-acetyltransferases, more specifically, AAC(6')-li and AAC(6')-ly, as well as compositions and uses thereof. Furthermore, the present invention relates to synthetic methodologies for preparing the inhibitors of aminoglycoside 6'-N-acetyltransferases.

11 Claims, 11 Drawing Sheets

OTHER PUBLICATIONS

Grapsas et al., "N-(tert-Butoxycarbonyloxy)-5-norbornene-endo-2,3-dicarboximide, a Reagent for the Regioselective Introduction of the tert-Butoxycarbonyl (BOC) Protective Group at Unhindered Amines: Application to Aminoglycoside Chemistry," *J. Org. Chem.*, 59:1918-1922, 1994.

Greenberg et al., "Design and Synthesis of New Aminoglycosides Containing Neamine as an Optical Core Structure: Correlation of Antibiotic Activity with in Vitro Inhibition of Translation," *J. Am. Chem. Soc.*, 121:6527-6541, 1999.

Haddad et al., "Design of novel antibiotics that bind to the ribosomal acyltransfer site," *J. Am. Chem. Soc.*, 124:3229-3237, 2002.

Hanessian and Patil, "Aminoglycoside Antibiotics—A Method for Selective N-Acylation Based on the Temporary Protection of Amino Alcohol Functions as Copper Chelates," *Tet. Lett.*, 12:1035-1038, 1978.

Hanessian et al., "Design, modeling and synthesis of functionalized paromamine analogs," *Tetrahedron*, 57:3255-3265, 2001.

Hanessian et al., "Tobramycin analogues with C-5 aminoalkyl ether chains intended to mimic rings III and IV of paromomycin," *Tetrahedron*, 59:983-993, 2003.

Hermann, "Strategies for the Design of Drugs Targeting RNA and RNA-Protein Complexes," *Chem. Int. Ed.*, 39:1890-1905, 2000.

Hermanson, "The Chemistry of Reactive Groups," *In: Bioconjugate Techniques*, Ch. 2., pp. 137-168, Academic Press, Inc, 1995.

Kim and Cole, "Bisubstrate Ketone Analogues as Serotonin N-Acetyltransferase Inhibitors," *J. Med. Chem.*, 44:2479-2485, 2001.

Li et al., "Role of the acetyltransferase AAC(6')-Iz modifying enzyme in aminoglycoside resistance in *Stenotrophomonas maltophilia*," *Antimicrob. Chemother.*, 51:803-811, 2003.

Litovchick et al., "Aminoglycoside- Arginine Conjugates That Bind TAR RNA: Synthesis, Characterization, and Antiviral Activity," *Biochemistry*, 39:2838-2852, 2000.

Liu et al., "Deoxystreptamine dimers bind to RNA hairpin loops," *J. Am. Chem. Soc.*, 126:9196-9197, 2004.

Luedtke et al., "RNA- Ligand Interactions: Affinity and Specificity of Aminoglycoside Dimers and Acridine Conjugates to the HIV-1 Rev Response Element," *Biochemistry*, 39:11391-11403, 2003.

Magnet et al., "Aminoglycoside Resistance Resulting from Tight Drug Binding to an Altered Aminoglycoside Acetyltransferase," *Antimicrobial Agents Chemother.*, 47:1577-1583, 2003.

Magnet et al., "Kinetic and Mutagenic Characterization of the Chromosomally Encoded *Salmonella enterica* AAC(6')-Iy Aminoglycoside N-Acetyltransferase," *Biochemistry*, 40:3700-3709, 2001.

Marmorstein, "Structure of Histone Acetyltransferases," *J. Mol. Biol.*, 311:433-444, 2001.

Michael et al., "Enhanced RNA Binding of Dimerized Aminoglycosides," *Bioorg. Med. Chem. Lett.*, 7:1361-1371, 1999.

Moiseev et al., "alpha-Halo Ketones in C-, N-, O-, and S-Alkylation Reactions," *Russian J. Org. Chem.*, 39:1685-1701, 2003.

Murray, "The life and times of the *Enterococcus*," *Clin. Microbiol. Rev.*, 3:46-65, 1990.

Nunns et al., "Synthesis of neamine libraries for RNA recognition using solution phase chemistry," *Tet. Lett.*, 40:9341-9345, 1999.

Park et al., "Rapid Combinatorial Synthesis of Aminoglycoside Antibiotic Mimetics: Use of a Polyethylene Glycol-Linked Amine and a Neamine-Derived Aldehyde in Multiple Component Condensation as a Strategy for the Discovery of New Inhibitors of the HIV RNA Rev Responisve Element," *J. Am. Chem. Soc.*, 118:10150-10155, 1996.

Perrey and Uckun, "An improved method for cysteine alkylation," *Tet. Lett.*, 42:1859-1861, 2001.

Poux et al., "Structure of the GCN5 histone acetyltransferase bound to a bisubstrate inhibitor," *Proc. Nat. Acad. Sci. USA*, 99:14065-14070, 2002.

Recht et al., "Basis for prokaryotic specificity of action of aminoglycoside antibiotics," *EMBO J.*, 18:3133-3138, 1999.

Roestamadji and Mobashery, "The use of neamine as a molecular template: inactivation of bacterial antibiotic resistance enzyme aminoglycoside 3'-phosphotransferase type IIa," *Bioorg. Med. Chem. Lett.*, 8:3483-3488, 1998.

Roestamadji et al., "Loss of Individual Electrostatic Interactions between Aminoglycoside Antibiotics and Resistance Enzymes as an Effective Means to Overcoming Bacterial Drug Resistance," *J. Am. Chem. Soc.*, 117:11060-11069, 1995.

Russell et al., "The Complex of a Designer Antibiotic with a Model Aminoacyl Site of the 30S Ribosomal Subunit Revealed be X-ray Crystallography," *J. Am. Chem. Soc.*, 124:3410-3411, 2003.

Ryu et al., "Stereospecificity of Aminoglycoside-Ribosomal Interactions," *Biochemistry*, 41:10499-10509, 2002.

Sagar et al., "Bisubstrate analogue structure-activity relationships for p300 histone acetyltransferase inhibitors," *Bioorg. Med. Chem.*, 12:3383-3390, 2004.

Sainlos et al., "Aminoglycoside-Derived Cationic Lipids for Gene Transfection: Synthesis of Kanamycin A Derivatives," *Eur. J. Org. Chem.*, 2764-2774, 2003.

Seeberger et al., "Synthesis of Neomycin Analogs to Investigate Aminoglycoside-RNA Interactions," *Synlett.*, 9:1323-1326, 2003.

Sucheck et al., "Design of Bifunctional Antibiotics that Target Bacterial rRNA and Inhibit Resistance-Causing Enzymes," *J. Am. Chem. Soc.*, 122:5230-5231, 2000.

Tok and Bi, "Aminoglycoside and its Derivatives as Ligands to Target the Ribosome," *Curr. Topics Med. Chem.*, 3:1001-1019, 2003.

Tok et al., "Aminoglycoside Hybrids as Potent RNA Antagonists," *Tetrahedron*, 55:5741-5758, 1999.

Vakulenko and Mobashery, "Versatility of aminoglycosides and prospects for their future," *Clin. Microbiol. Rev.*, 16:430-450, 2003.

Van Schepdael et al., "The Selective Protection of Amino Functions in Aminoglycosides: A Review of Possible Approaches," *Soc. Chim. Belg., Eur. Section*, 101:709-718, 1992.

Venot et al., "Disaccharide mimetics of the aminoglycoside antibiotic neamine," *Chem. Bio. Chem.*, 5:1228-1236, 2004.

Verhelst et al., "Glycosylation of Cyclitols: Synthesis of Neamine-Tupe Aminoglycosides," *Eur. J. Org. Chem.*, 2404-2410, 2004.

Vicens and Westhof, "Molecular Recognition of Aminoglycoside Antibiotics by Ribosomal RNA and Resistance Enzymes: An Analysis of X-Ray Crystal Structures," *Biopolymers*, 70:42-57, 2003.

Walsh, "Where will new antibiotics come from?," *Nat. Rev. (Microbiology)*, 1:65-70, 2003.

Wang and Tor, "Electrostatic Interactions in RNA Amionglycosides Binding," *J. Am. Chem. Soc.*, 119:8734-8735, 1997.

Wang et al., "Specificity of Aminoglycoside Binding to RNA Constructs Derived from the 16S rRNA Decoding Region and the HIV-RRE Activator Region," *Biochemistry*, 36:768-779, 1997.

Williams and Northrop, "Kinetic mechanisms of gentamicin acetyltransferase I. Antibiotic-dependent shift from rapid to nonrapid equilibrium random mechanisms," *J. Biol. Chem.*, 253:5902-5907, 1978.

Williams and Northrop, "Synthesis of a tight-binding, multisubstrate analog inhibitor of gentamicin acetyltransferase I," *J. Antibiotic*, 32:1147-1154, 1979.

Wright and Ladak, "Overexpression and Characterization of the Chromosomal Aminoglycoside 6'-N-Acetyltransferase from *Enterococcus faecium*," *Antimicrobial Agents and Chemotherapy*, 41:956-960, 1997.

Wright et al., "Aminoglycoside Antibiotics," In: *Resolving the Antibiotic Paradox*, Rosen and Mobashery (Eds.), Kluwer Academic/Plenum Publishers, NY, 27-69, 1998.

Wright, "Aminoglycoside-modifying enzymes," *Curr. Opin. Microbiol.*, 2:499-503, 1999.

Wybenga-Groot et al., "Crystal structure of an aminoglycoside 6'-N-acetyltransferase: defining the GCN5-related N-acetyltransferase superfamily fold," *Structure*, 7:497-507, 1999.

Yang et al., "Efficient Method for Regioselective Isoprenylation of Cysteine Thiols in Unprotected Peptides," *J. Am. Chem. Soc.*, 113:3177-3178, 1991.

Yao et al., "Glyco-optimization of aminoglycosides: new aminoglycosides as novel anti-infective agents," *J. Bioorg. Med. Chem. Lett.*, 14:3733-3738, 2004.

Zheng and Cole, "Novel bisubstrate analog inhibitors of serotonin N-acetyltransferase: the importance of being neutral," *Bioorg. Chem.*, 31:398-411, 2003.

* cited by examiner

INHIBITORS OF AMINOGLYCOSIDE 6'-N-ACETYLTRANSFERASES, COMPOSITIONS AND USES THEREOF

The present application claims the benefit of provisional Application No. 60/653,979 filed Feb. 18, 2005, the entire contents of which is incorporated by reference.

FIELD OF THE INVENTION

The present invention relates to inhibitors of aminoglycoside 6'-N-acetyltransferases as well as to compositions and uses thereof.

BACKGROUND OF THE INVENTION

Aminoglycosides are among the most commonly used broad-spectrum antibiotics. They are often used in combination with other antibiotics, such as β-lactams, as the first line of defense against serious infections caused particularly by various gram-negative bacteria (Wrght et al., 1998; Coates et al., 2002; Vakulenko and Mobashery, 2003). Structurally, aminoglycosides most often comprise a central 2-deoxystreptamine aminocyclitol ring to which amino sugars are linked by means of α-glycosidic bonds either at positions 4 and 5 (e.g. neomycin B) or at positions 4 and 6 (e.g. gentamicin $C_1$) (FIG. 1).

At physiological pH, the amino groups of aminoglycosides are protonated to yield polycations that bind to the major groove of polyanionic 16S rRNA (on the 30S ribosome) of prokaryotic cells (Recht et al., 1999; Fourmy et al., 1997; Fourmy et al., 1998), thereby impeding the synthesis of bacterial proteins. The high level of affinity between aminoglycosides and RNA is more likely the result of nonspecific electrostatic interactions (Wang and tor, 1997; Roestamadji et al., 1995), whereas the specificity of aminoglycosides is believed to be determined by hydrogen bonding between the RNA and the upper two rings of the aminoglycosides (Vicens and Westhof, 2003; Ryu et al., 2002).

Recently, increasing evidence has suggested that RNA may become a prime target for antiviral therapy (gallego and Varani, 2001; Hermann, 2000), as supported by a growing interest for small molecules capable of interfering with RNA. Among these small molecules, aminoglycosides are arguably the most studied and best characterized. Aminoglycosides have become leading structures for studying RNA-ligand interactions as well as for designing novel ligands for nucleotides (Tok et al., 2003; Seeberger et al., 2003). Many aminoglycoside derivatives have shown antiviral activity by binding to specific regions of viral RNA (Luedtke et al., 2003; Arya et al., 2004; Liu et al., 2004; Litovchick et al., 2000).

One of the many features of aminoglycosides resides in their ability to recognize secondary and tertiary structures of RNA in which the base pairing has been disrupted (e.g. bulges, internal loops and stem junctions). A specific example of such secondary and tertiary structures constitutes the bulge regions of unrelated RNA sequences from the 16S ribosome, HIV TAR, HIV RRE, and the Group I intron (Wang et al., 1997; Arya et al., 2001; Arya et al., 2001). Furthermore, aminoglycosides specifically bind to kissing-loop complexes formed by the RNA dimerization initiation site of the HIV virus (Russell et al., 2003), stabilize DNA-RNA triplexes and hybrid duplexes, and even induce hybrid triplex formation (Sucheck et al., 2000; Arya et al., 2003). The use of aminoglycosides as antiviral agents has been previously suggested.

The rapid emergence of bacterial resistance to aminoglycoside antibiotics is severely limiting their use and mitigating clinical efficacy in severe bacterial infections, thus creating a pressing need for the discovery and development of structurally novel and more potent antibiotics (Walsh, 2003). One alternative to circumvent bacterial resistance is through derivatization of existing antibiotics (Tok et al., 2003; Seeberger et al., 2003; Hanessian et al., 2003; Hanessian et al., 2001; Yao et al., 2004; Venot et al., 2004).

Derivatization of specific functional groups often prevents inactivation of aminoglycosides by enzymes without compromising their antibacterial activity (Tok et al., 1999). For example, dimerization of aminoglycosides has led to better activity against resistant strains (Agnelli et al., 2004; Michael et al., 1999). Naturally occurring aminoglycosides are complex molecules, often difficult to modify chemically. The judicious protection of functional groups is critical to selective derivatization, but is time consuming ((Haddad et al., 2002; Roestamadji and Mobashery, 1998). Wong and others have developed a strategy based on the neamine scaffold and azido chemistry, to generate several neamine-based aminoglycoside analogs that have shown good antibacterial activity against resistant strains (Hanessian et al., 2003; Hanessian et al., 2001; Yao et al., 2004; Venot et al., 2004; Haddad et al., 2002; Roestamadji and Mobashery, 1998; Alper et al., 1996; Chou et al., 2004; Greenberg et al., 1999; Park et al., 1996; Ding et al., 2003; Ding et al., 2000; Verhelst et al., 2004). In spite of the recent advancements, regioselective modifications of aminoglycosides remain challenging.

A second option aimed at overcoming antibiotic resistance involves the elimination of the resistance-causing processes. Inhibiting the enzymes responsible for causing drug resistance has proven to be a valuable approach to overcome bacterial resistance. The combination of a β-lactamase inhibitor (clavulinate) and β-lactam antibiotics, has become a front line therapy for fighting β-lactam resistant bacteria (Draker and Wright, 2004; Draker et al., 2003).

Bacterial resistance to aminoglycosides occurs via mutation of the ribosome, drug efflux and most commonly via conjugation of the aminoglycoside drug by specific bacterial enzymes (Vakulenko and Mobashery, 2003; Azucena and Mobashery, 2001; Wright, 1999). The latter may arise via pathways including acetylation, adenylation or phosphorylation. These structural modifications reduce the antibiotic activity of aminoglycosides by decreasing their binding affinity for bacterial RNA.

Of the different groups of enzymes leading to aminoglycoside resistance, aminoglycoside 6'-N-acetyltransferases [AAC(6')s] are of particular interest. This group of enzymes acts by transferring an acetyl group from acetyl coenzyme A (AcCoA) to the 6'-$NH_2$ of a number of aminoglycosides.

In clinical isolates of aminoglycoside-resistant strains, N-acetyltransferase is the most frequently observed cause of resistance (Wright and Ladak, 1997). Examples of known AAC(6')s include, but are not limited to AAC(6')-Ii (Wright and Ladak, 1997), AAC(6')-APH(2") (Boehr et al., 2004), AAC(6')-Ie (Culebras and Martinez, 1999), AAC(6')-Iy (Magnet et al., 2001), AAC(6')-29b (Magnet et al., 2003), and AAC(6')-Iz (Li et al., 2003).

Bi-substrate analogues have been previously used for the design of inhibitors of serotonin acetyltransferase (Kim and Cole, 2001) and GCN5 histone acetyltransferase (Poux et al., 2002; Sagar et al., 2004). Williams et al. have described the gentamicin acetyltransferase I catalyzed acyl transfer to generate exclusively 3-N-chloroacetylgentamycin, which is subsequently converted to gentamicyl-3-N-acetyl CoA (Williams and Northrop, 1979).

There thus remains a need for inhibitors of aminoglycoside 6'-N-acetyltransferases. More specifically, there remains a need for inhibitors of aminoglycoside 6'-N-acetyltransferases capable of reversing or inhibiting bacterial resistance to aminoglycoside antibiotics.

The present invention seeks to meet these and other needs.

The present description refers to a number of documents, the content of which is herein incorporated by reference in their entirety.

SUMMARY OF THE INVENTION

The present invention relates to novel inhibitors of aminoglycoside 6'-N-acetyltransferases. More specifically, but not exclusively, the present invention relates to novel inhibitors of aminoglycoside 6'-N-acetyltransferases capable of inhibiting bacterial resistance to aminoglycoside antibiotics. In an embodiment, the present invention relates to novel inhibitors of AAC(6')-Ii and AAC(6')-Iy. In a further embodiment, the present invention relates to synthetic methodologies for prepraring novel inhibitors of aminoglycoside 6'-N-acetyltransferases.

In an embodiment, the present invention relates to an inhibitor of aminoglycoside 6'-N-acetyltransferases of Formula I:

R—X—Y—Z           Formula I wherein:
R is selected from the group consisting of

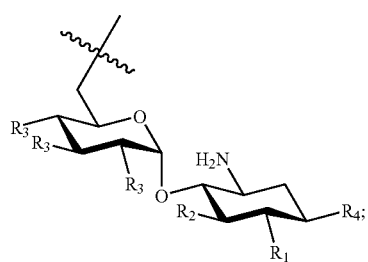

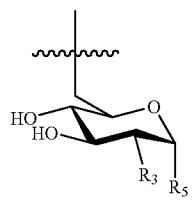

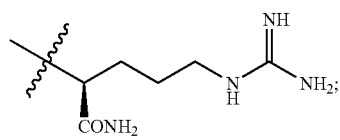

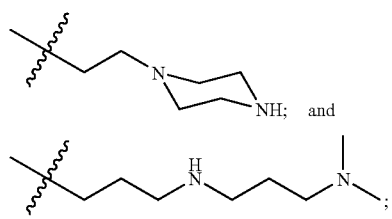

$R_1$ is selected from the group consisting of OH and

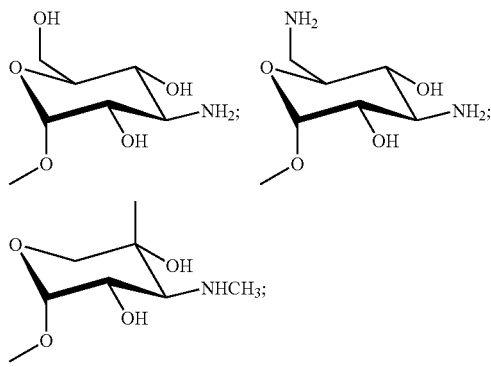

$R_2$ is selected from the group consisting of OH and

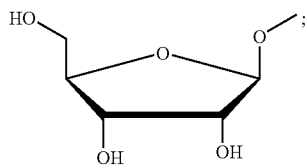

$R_3$ is selected from the group consisting of $NH_2$ and OH;
$R_4$ is selected from the group consisting of $NH_2$ and
$R_5$ is

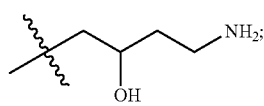

selected from the group consisting of OMe, OEt OPr, and O-iPr;
X is selected from the group consisting of NH and O;
Y is selected from the group consisting of.

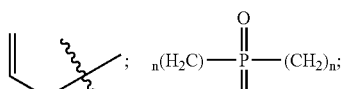

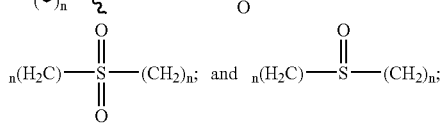

$R_6$ is selected from the group consisting of OH, $CH_3$, and $OCH_3$;
n is an integer ranging from 1 to 10;
Z is selected from the group consisting of

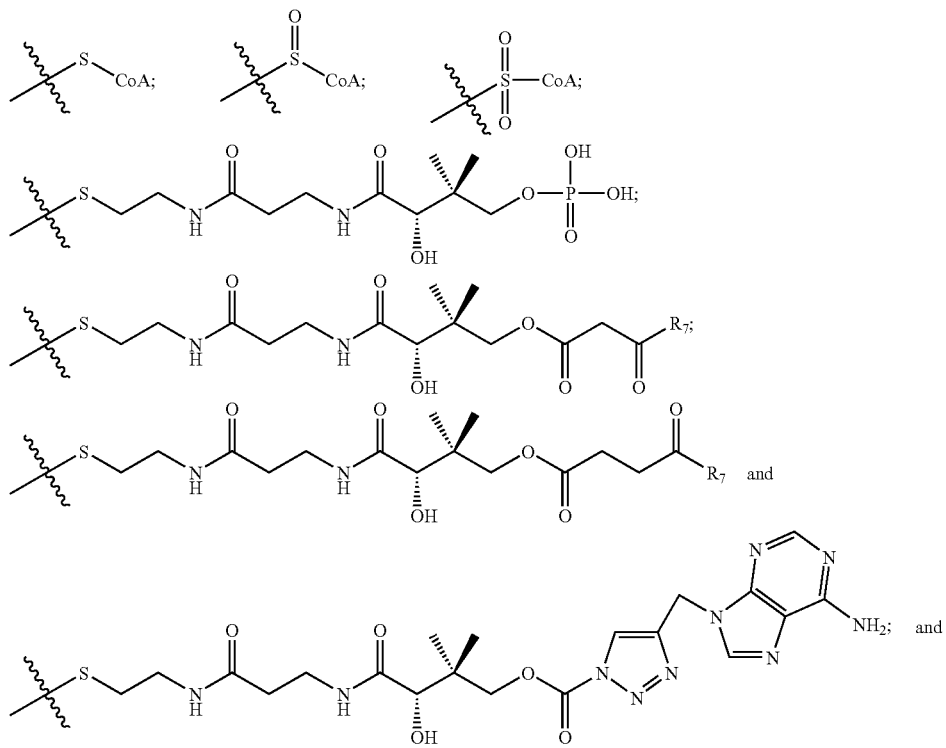

R$_7$ is selected from the group consisting of OH, OMe, OEt OPr, O-iPr, O-tBu and

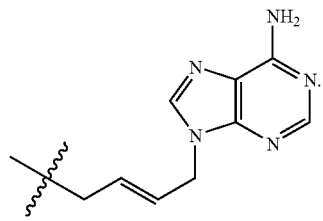

In an embodiment, the present invention relates to a pharmaceutical formulation for inhibiting bacterial resistance to aminoglycoside antibiotics comprising a pharmaceutically effective amount of at least one inhibitor of aminoglycoside 6'-N-acetyltransferases as defined herein, in association with a pharmaceutically acceptable carrier, excipient and/or diluent.

In an embodiment, the present invention relates to an admixture comprising at least one inhibitor of aminoglycoside 6'-N-acetyltransferases as defined herein, in association with one or more pharmaceutically acceptable carriers, excipients and/or diluents.

In an embodiment, the present invention relates to a use of an inhibitor of aminoglycoside 6'-N-acetyltransferases as defined herein, for the manufacture of a medicament for treating or preventing a disease or condition associated with bacterial resistance to aminoglycoside antibiotics.

In an embodiment, the present invention relates to an admixture comprising at least one inhibitor of aminoglycoside 6'-N-acetyltransferases as defined herein, in association with one or more antibacterial agents and one or more pharmaceutically acceptable carriers, excipients and/or diluents.

The foregoing and other objects, advantages and features of the present invention will become more apparent upon reading of the following non restrictive description of illustrative embodiments thereof, given by way of example only with reference to the accompanying drawings.

DETAILED DESCRIPTION

Figure 1:
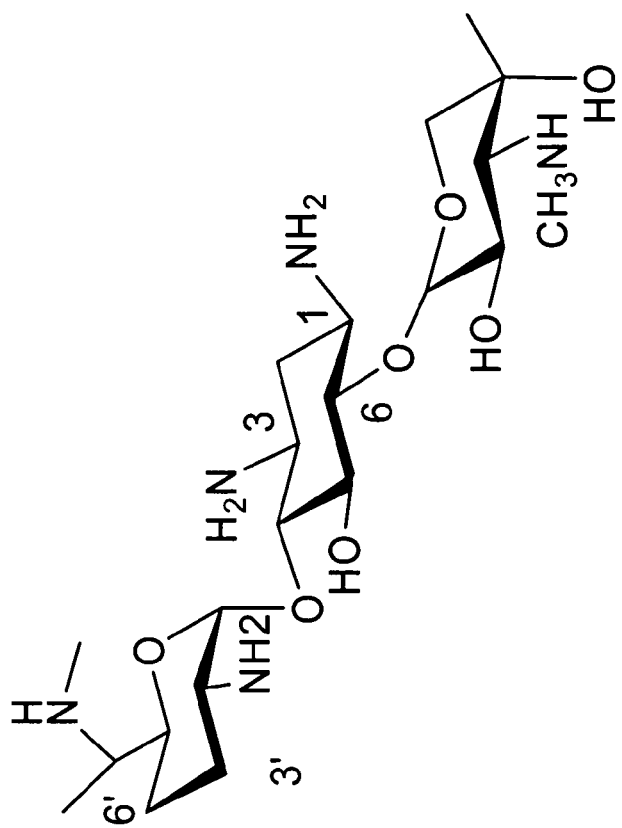
FIG. 1 is an illustration of the chemical structure of Neomycin B and Gentamicin C$_1$.
Figure 1:
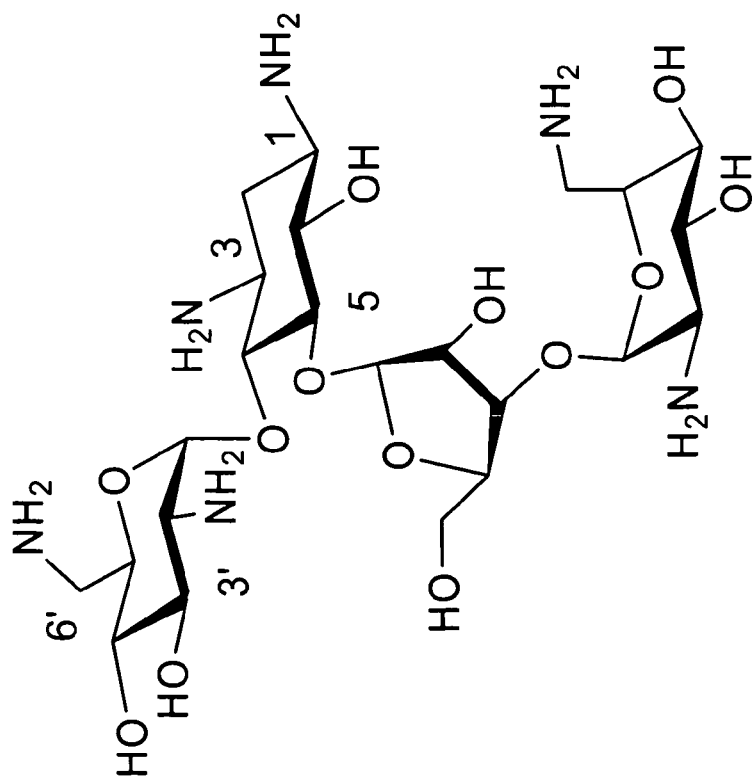
Figure 2:
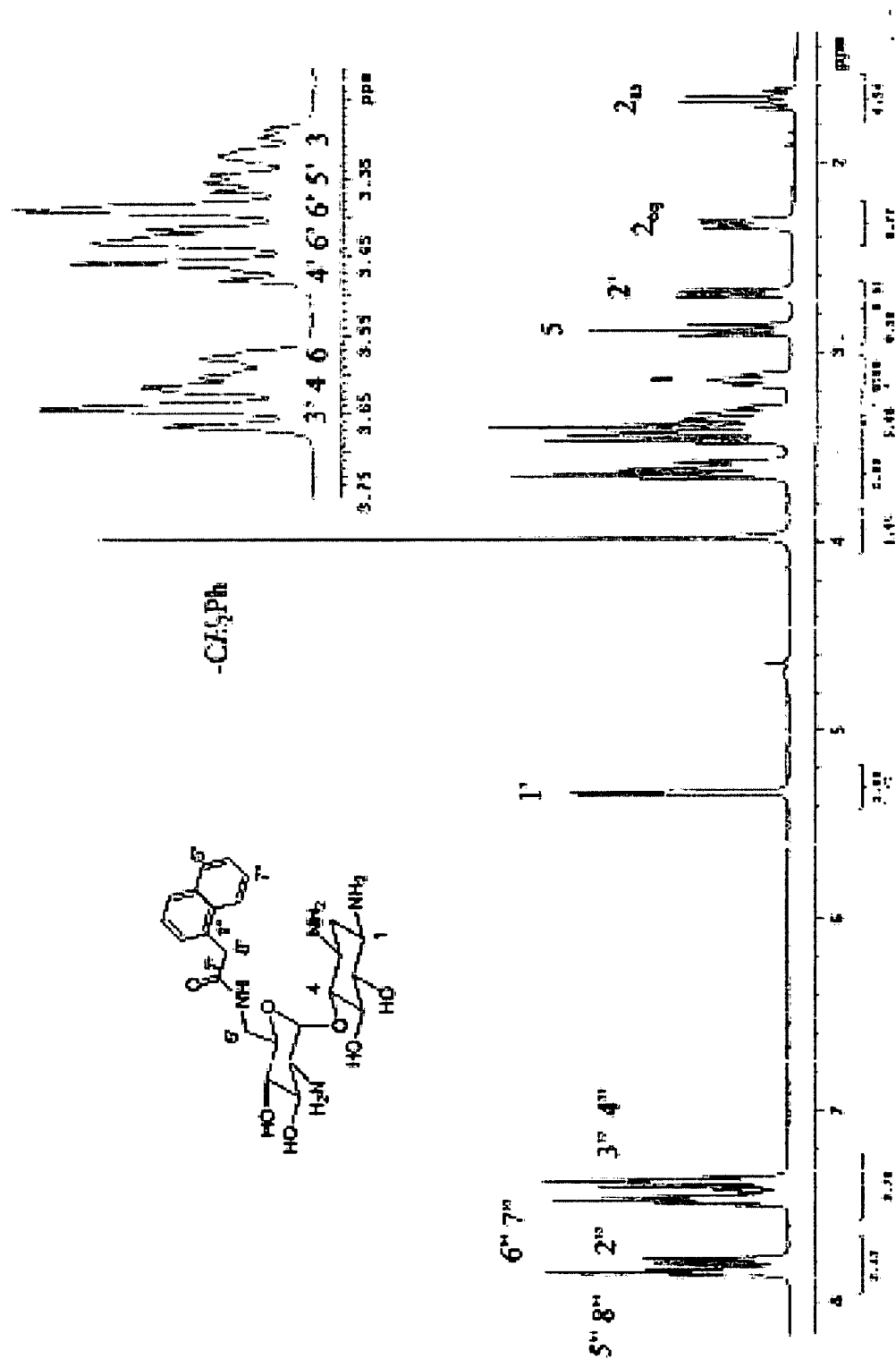
FIG. 2 is an illustration of the $^1$H NMR spectrum of compound 6f in accordance to an embodiment of the inhibitors of aminoglycoside 6'-N-acetyltransferases of the present invention.
Figure 3:
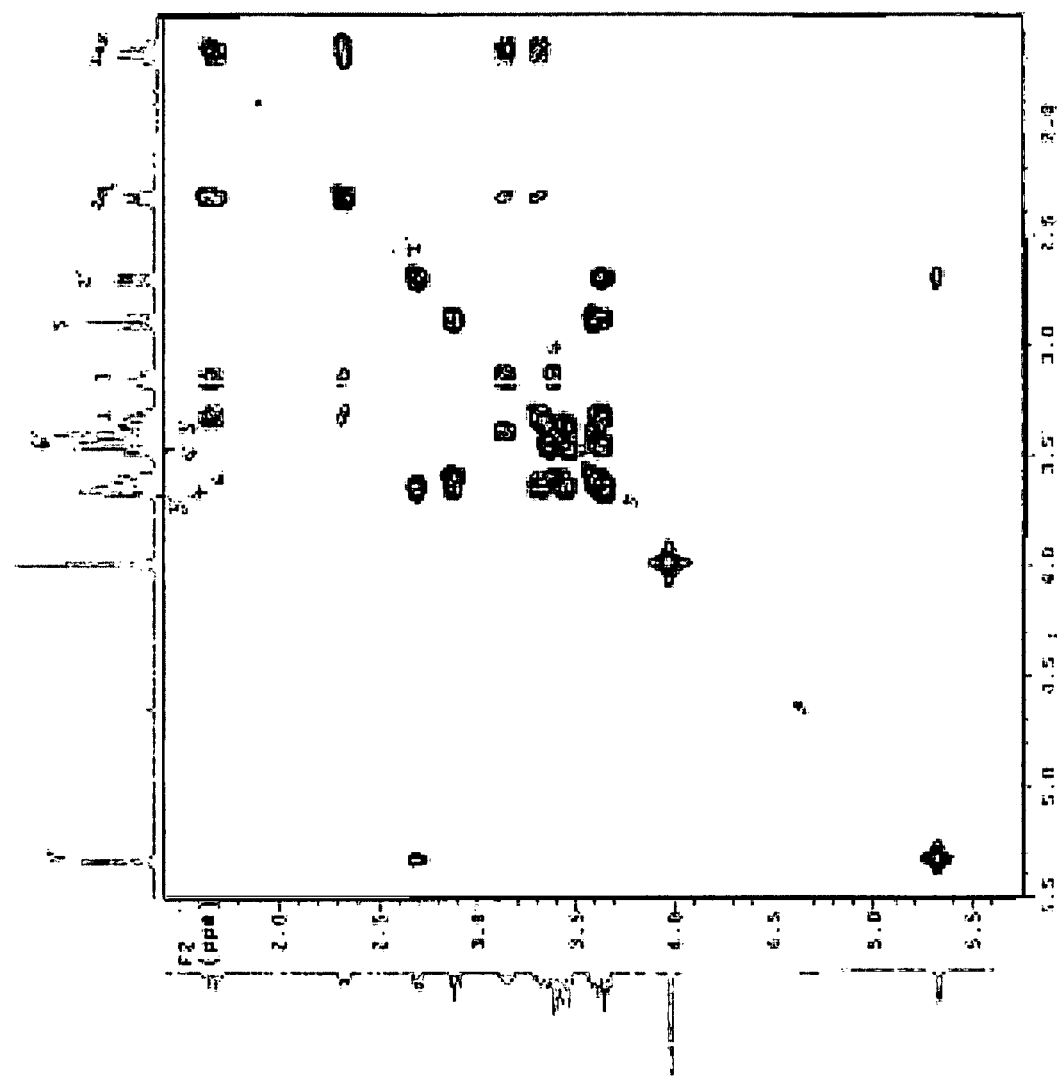
FIG. 3 is an illustration of the $^1$H-$^1$H COSY spectrum of compound 6f in accordance to an embodiment of the inhibitors of aminoglycoside 6'-N-acetyltransferases of the present invention.
Figure 4:
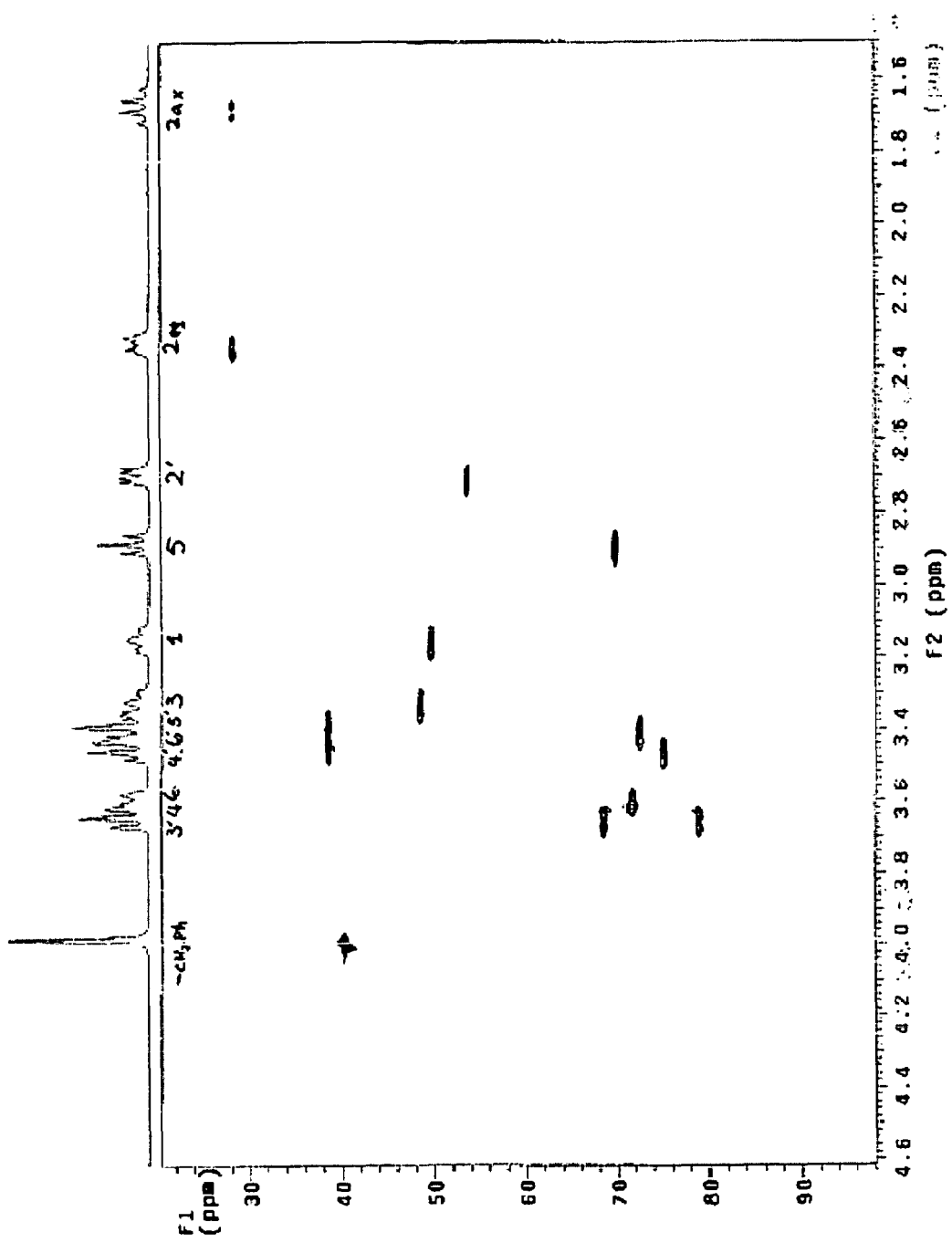
FIG. 4 is an illustration of the $^1$H-$^{13}$C HSQC spectrum of compound 6f in accordance to an embodiment of the inhibitors of aminoglycoside 6'-N-acetyltransferases of the present invention.
Figure 5:
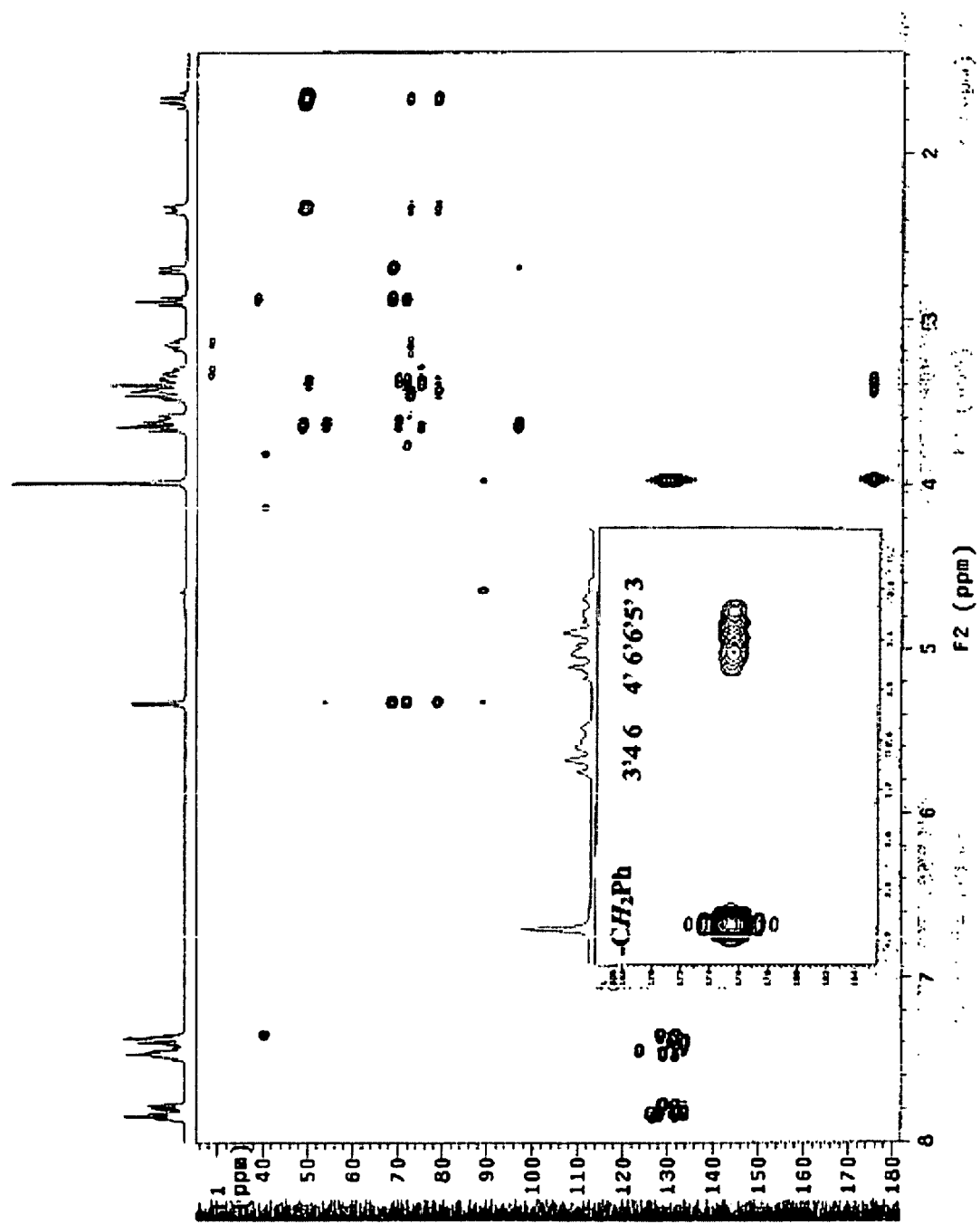
FIG. 5 is an illustration of the $^1$H-$^{13}$C HMBC spectrum of compound 6f in accordance to an embodiment of the inhibitors of aminoglycoside 6'-N-acetyltransferases of the present invention.
Figure 6:
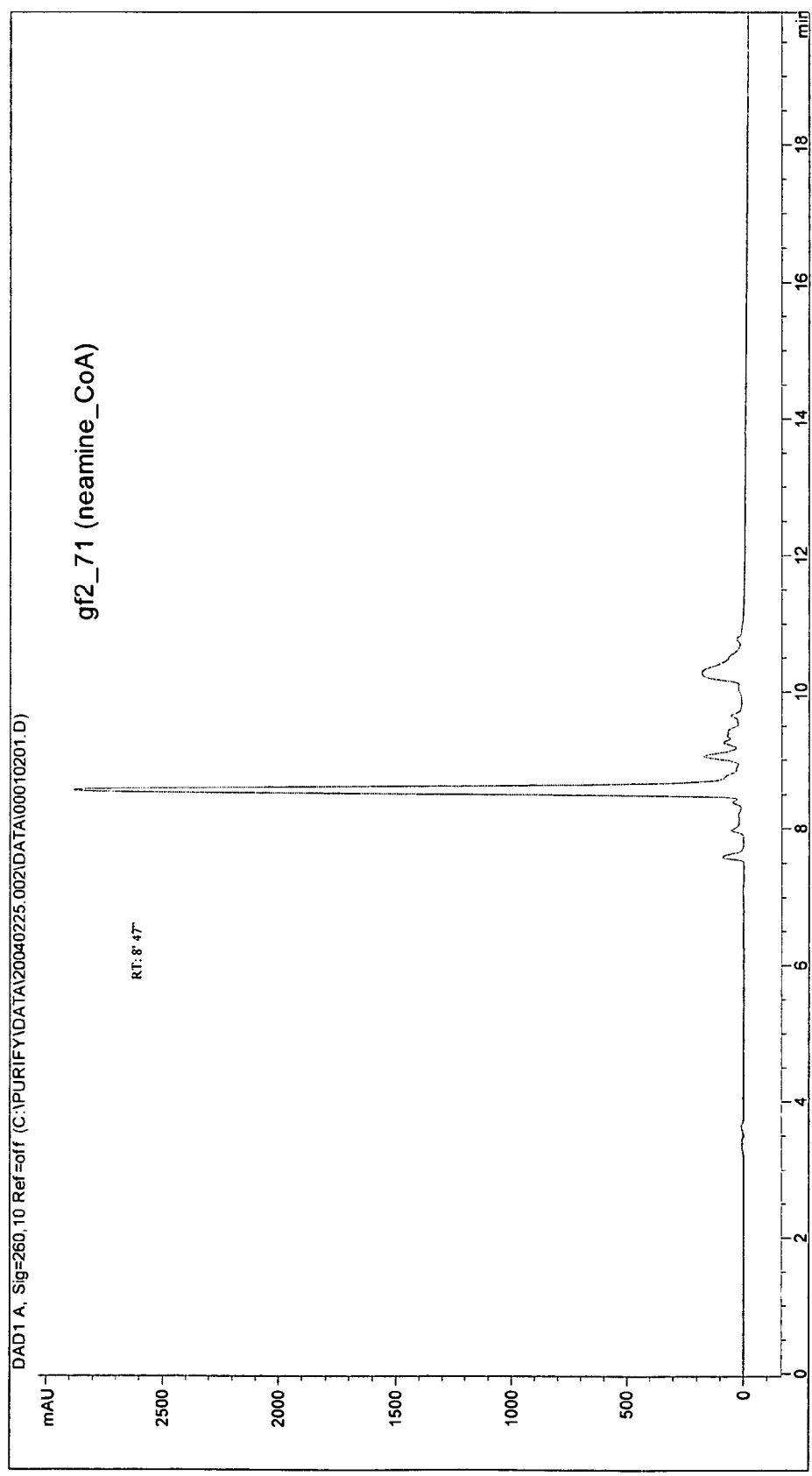
FIG. 6 is an illustration of the HPLC chromatogram of crude compound 10 in accordance to an embodiment of the inhibitors of aminoglycoside 6'-N-acetyltransferases of the present invention.
Figure 7:
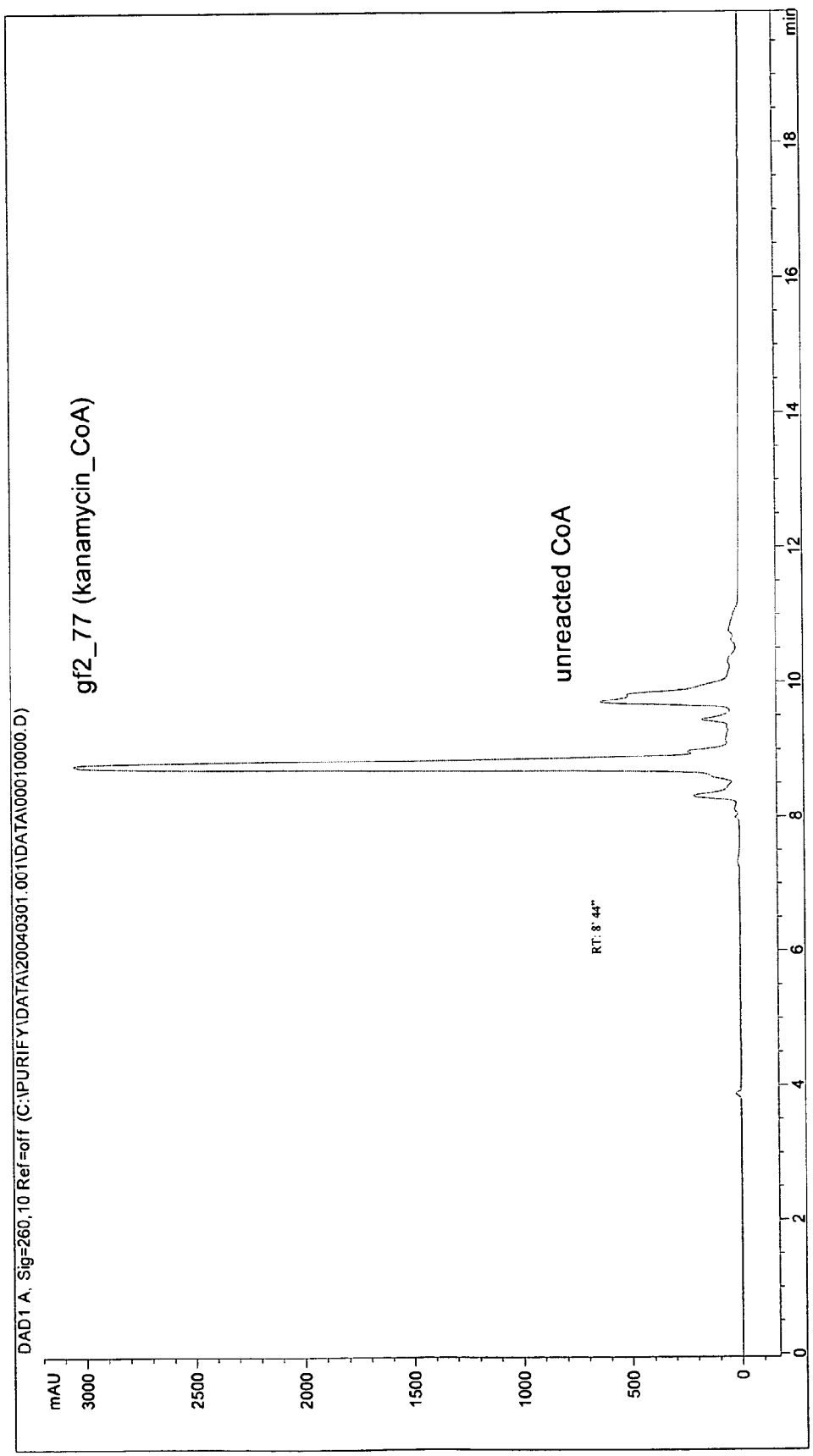
FIG. 7 is an illustration of the HPLC chromatogram of crude compound 11 in accordance to an embodiment of the inhibitors of aminoglycoside 6'-N-acetyltransferases of the present invention.
Figure 8:
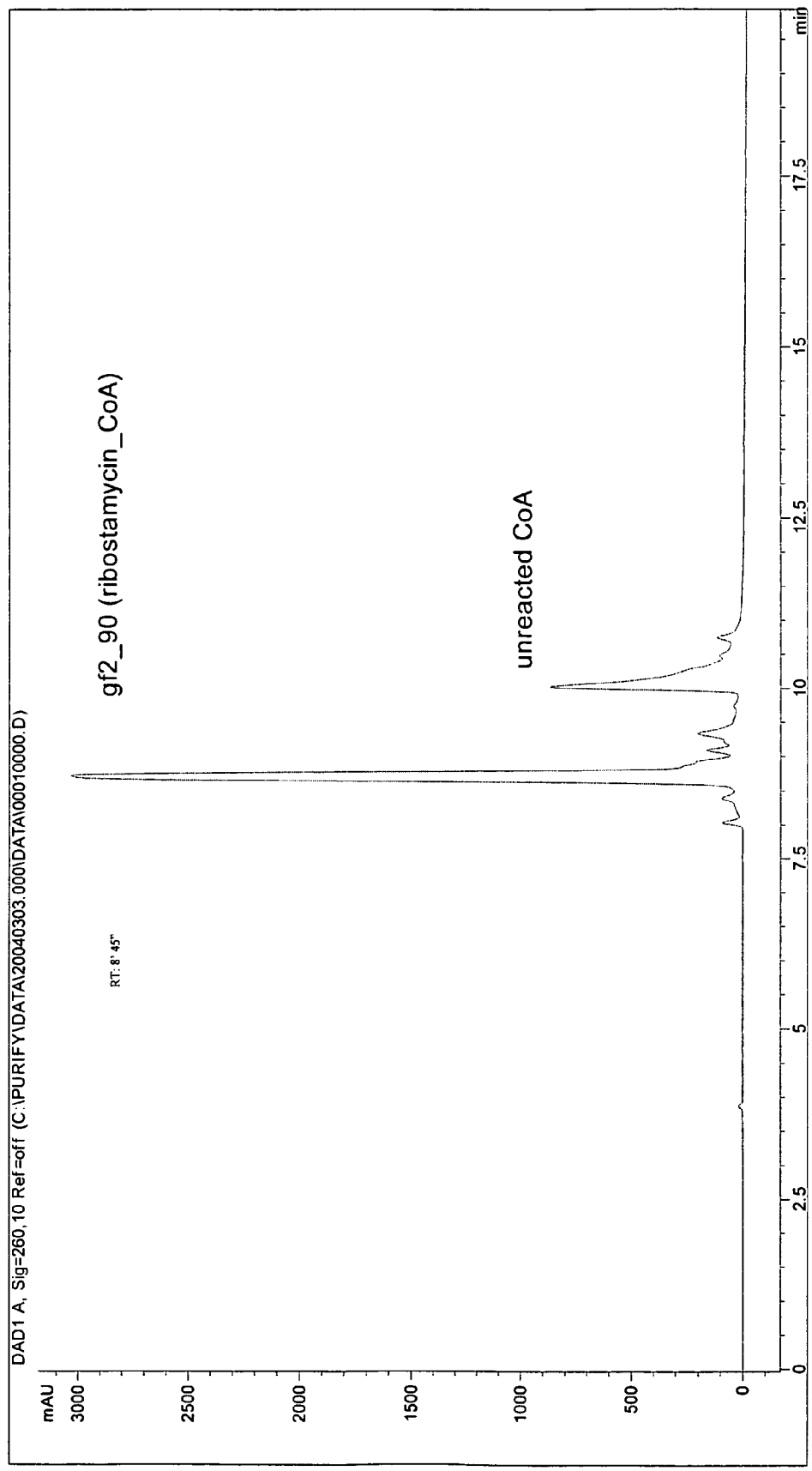
FIG. 8 is an illustration of the HPLC chromatogram of crude compound 12 in accordance to an embodiment of the inhibitors of aminoglycoside 6'-N-acetyltransferases of the present invention.
Figure 9:
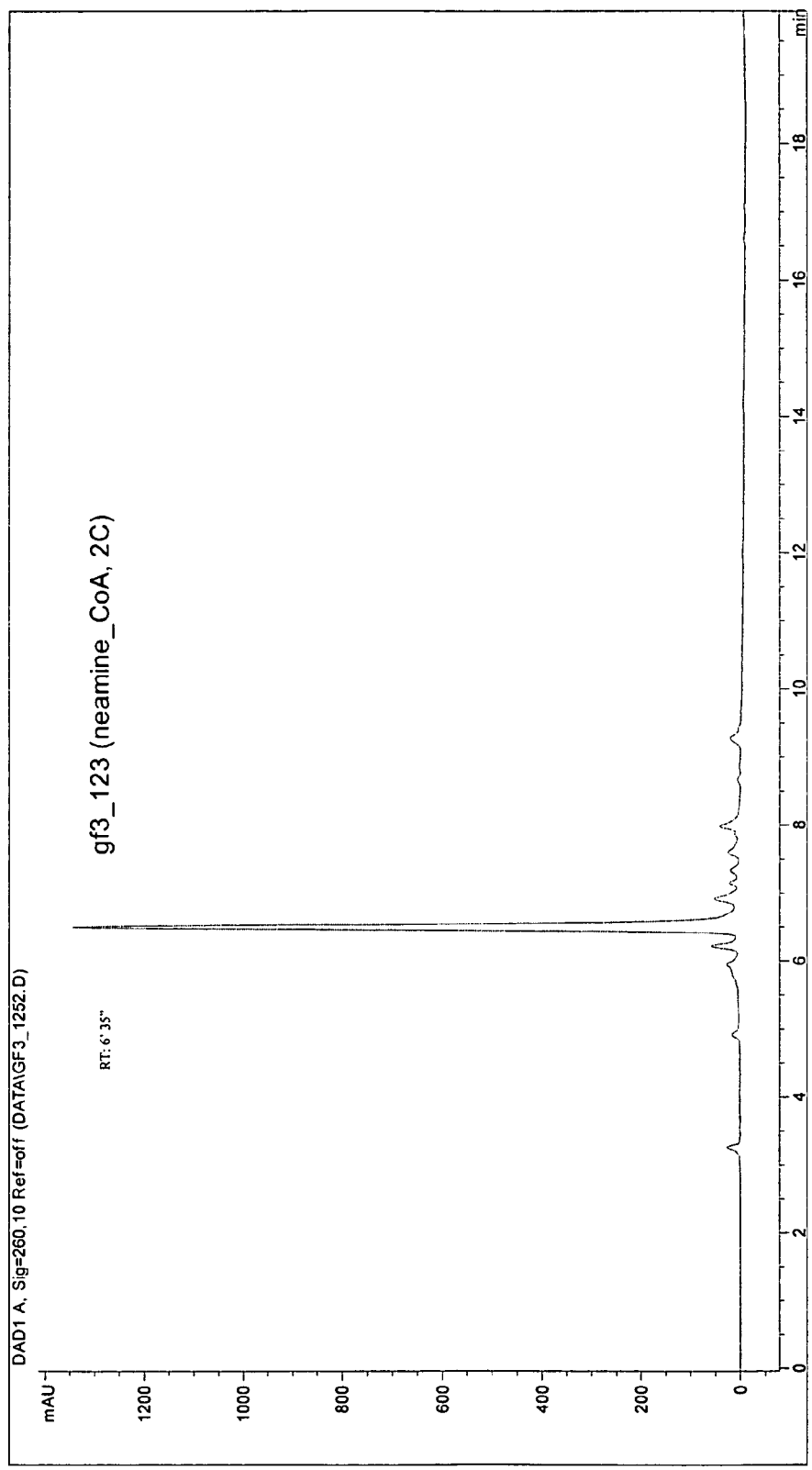
FIG. 9 is an illustration of the HPLC chromatogram of crude compound 14a in accordance to an embodiment of the inhibitors of aminoglycoside 6'-N-acetyltransferases of the present invention.
Figure 10:
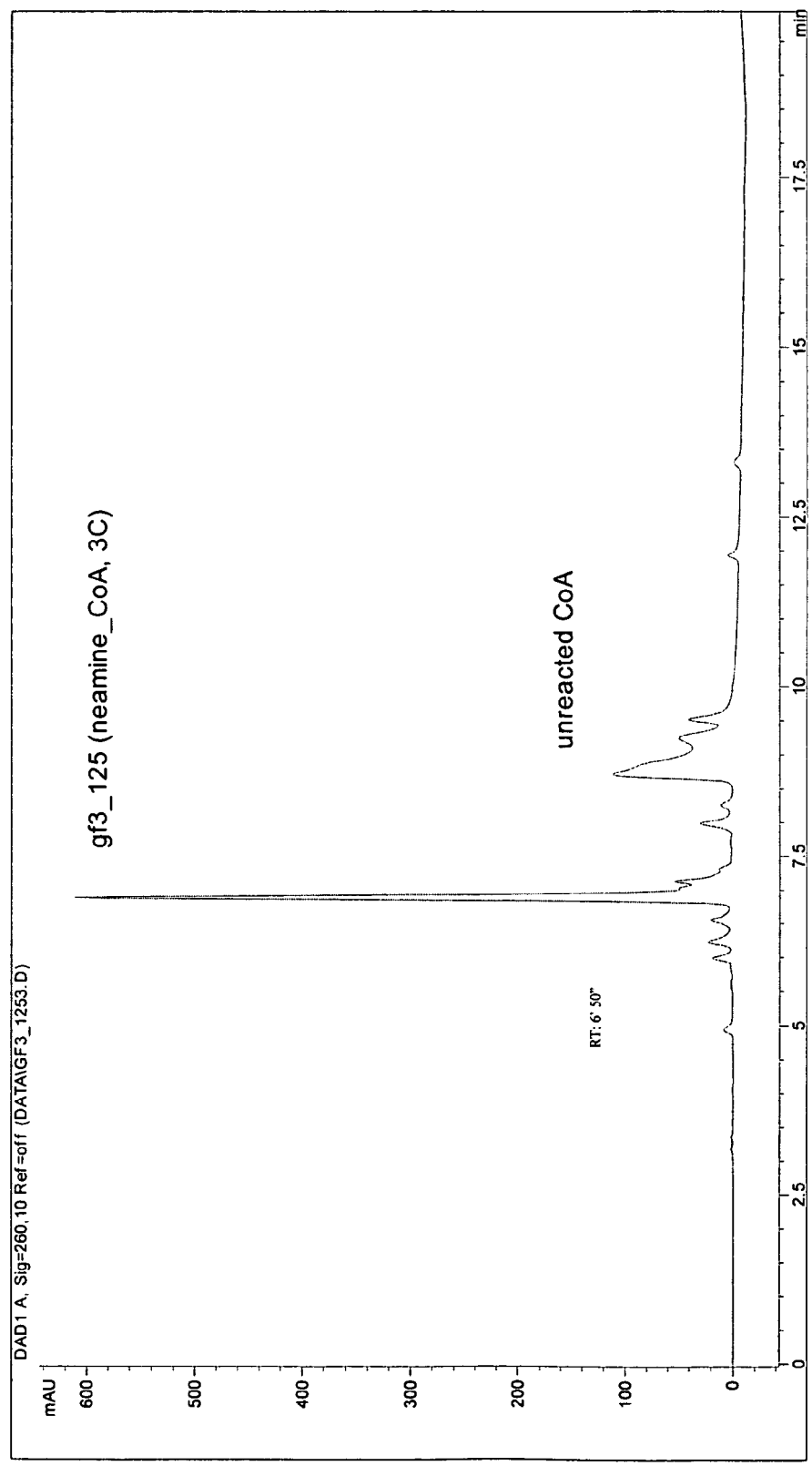
FIG. 10 is an illustration of the HPLC chromatogram of crude compound 14b in accordance to an embodiment of the inhibitors of aminoglycoside 6'-N-acetyltransferases of the present invention.
Figure 11:
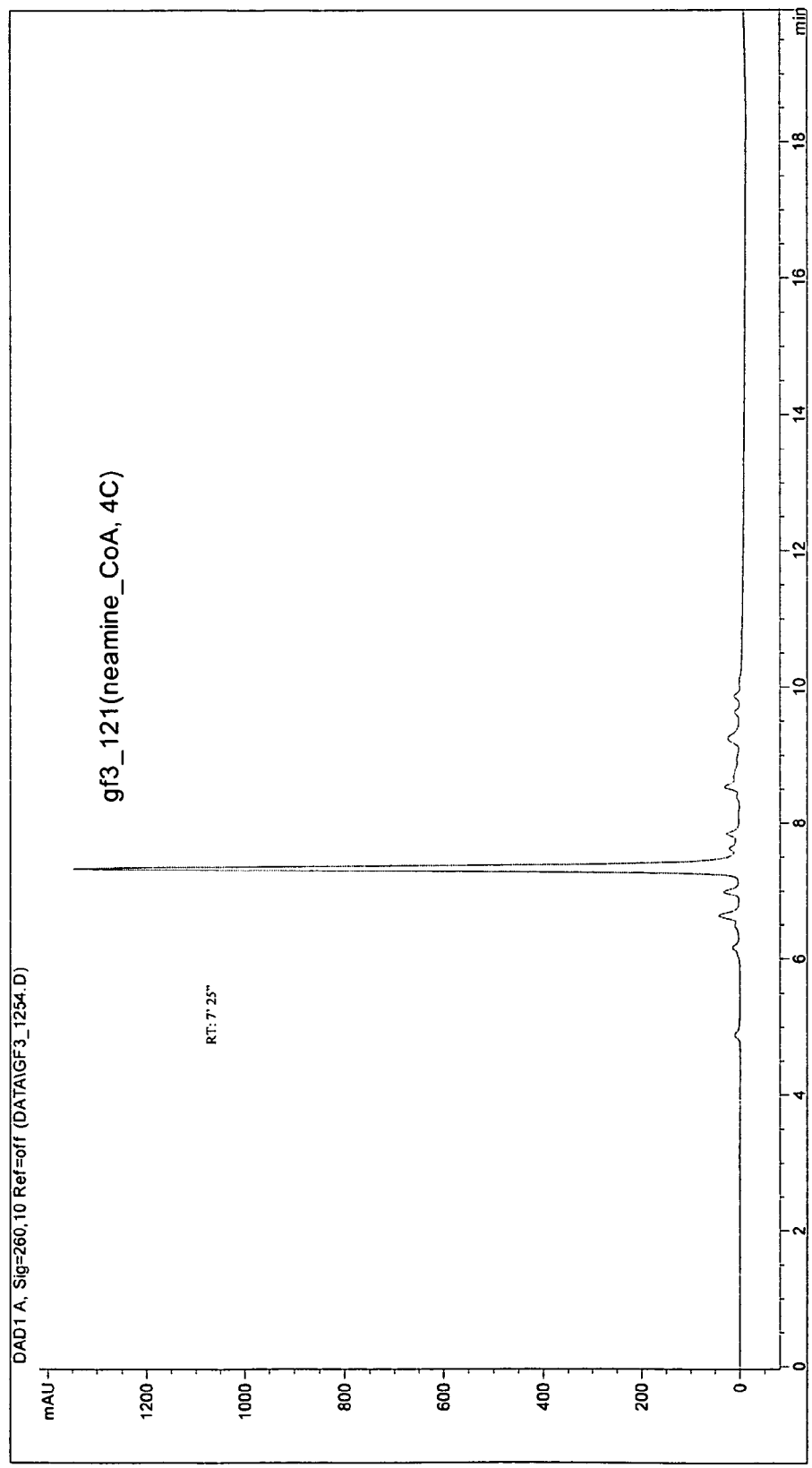
FIG. 11 is an illustration of the HPLC chromatogram of crude 14c in accordance to an embodiment of the inhibitors of aminoglycoside 6'-N-acetyltransferases of the present invention.

In order to provide a clear and consistent understanding of the terms used in the present specification, a number of definitions are provided below. Moreover, unless defined otherwise, all technical and scientific terms as used herein have the same meaning as commonly understood to one of ordinary skill in the art to which this invention pertains.

The use of the word "a" or "an" when used in conjunction with the term "comprising" in the claims and/or the specification may mean "one", but it is also consistent with the meaning of "one or more", "at least one", and "one or more than one". Similarly, the word "another" may mean at least a second or more.

As used in this specification and claim(s), the words "comprising" (and any form of comprising, such as "comprise" and "comprises"), "having" (and any form of having, such as "have" and "has"), "including" (and any form of including, such as "include" and "includes") or "containing" (and any form of containing, such as "contain" and "contains"), are inclusive or open-ended and do not exclude additional, unrecited elements or process steps.

The term "about" is used to indicate that a value includes an inherent variation of error for the device or the method being employed to determine the value.

The present description refers to a number of chemical terms and abbreviations used by those skilled in the art. Nevertheless, definitions of selected terms are provided for clarity and consistency.

Abbreviations: AcCoA: Acetyl Coenzyme A; ACN: Acetonitrile; APCI: Atmospheric Pressure Chemical Ionization; CoA: Coenzyme A; COSY: $^1$H-$^1$H Correlation Spectroscopy; DCC: 1,3-Dicyclohexylcarbodimide; DCM: Dichloromethane; DCU: 1,3-Dicyclohexylcarbodiurea; DMAP: N,N-Dimethylpyridine; DTDP: 4,4'-Dithiodipyridine; DTT: 1,4-Dithiothreitol; DIPEA (Hunig's base): Diisopropyl ethyl amine; EDTA: Ethylenediaminetetraacetic acid; ESI: Electron Spray Ionization; EtOAc: Ethyl acetate; HEPES: 4-(2-hydroxyethyl)-1-piperazineethanesulfonic acid; Hex: Hexane; HMBC: $^1$H-$^{13}$C Heteronucleus Multiple Bond Correlation Spectroscopy; HRMS: High Resolution Mass Spectrometry; HSQC: $^1$H-$^{13}$C Heteronucleus Single Quantum Correlation Spectroscopy; LB: Luria-Bertani media; TEA: Triethylamine; THF: Tetrahydrofuran; TLC: Analytical Thin Layer Chromatography; TOCSY: Total Correlation Spectroscopy.

In an embodiment, the present invention relates to pharmaceutical compositions comprising a pharmaceutically effective amount of one or more inhibitors of aminoglycoside 6'-N-acetyltransferases as defined herein, or pharmaceutically acceptable salts thereof, in association with one or more pharmaceutically acceptable carriers, excipients and/or diluents. The term "pharmaceutically effective amount" is understood as being an amount of inhibitor of aminoglycoside 6'-N-acetyltransferases required upon administration to a mammal in order to inhibit or reverse bacterial resistance. Therapeutic methods comprise the step of treating patients in a pharmaceutically acceptable manner with inhibitors of aminoglycoside 6'-N-acetyltransferases or compositions comprising inhibitors of aminoglycoside 6'-N-acetyltransferases as disclosed herein. Such compositions may be in the form of tablets, capsules, caplets, powders, granules, lozenges, suppositories, reconstitutable powders, or liquid preparations, such as oral or sterile parenteral solutions or suspensions.

The therapeutic agents of the present invention (i.e. inhibitors of aminoglycoside 6'-N-acetyltransferases) may be administered alone or in combination with pharmaceutically acceptable carriers. The proportion of each carrier is determined by the solubility and chemical nature of the agent(s), the route of administration, and standard pharmaceutical practice. In order to ensure consistency of administration, in an embodiment of the present invention, the pharmaceutical composition is in the form of a unit dose. The unit dose presentation forms for oral administration may be tablets and capsules and may contain conventional excipients. Non-limiting examples of conventional excipients include binding agents such as acacia, gelatin, sorbitol, or polyvinylpyrolidone; fillers such as lactose, sugar, maize-starch, calcium phosphate, sorbitol or glycine; tabletting lubricants such as magnesium stearate; disintegrants such as starch, polyvinylpyrrolidone, sodium starch glycollate or microcrystalline cellulose; or pharmaceutically acceptable wetting agents such as sodium lauryl sulphate.

The inhibitors of aminoglycoside 6'-N-acetyltransferases of the present invention may be injected parenterally; this being intramuscularly, intravenously, or subcutaneously. For parenteral administration, the inhibitors of aminoglycoside 6'-N-acetyltransferases may be used in the form of sterile solutions containing solutes, for example sufficient saline or glucose to make the solution isotonic.

The inhibitors of aminoglycoside 6'-N-acetyltransferases maybe administered orally in the form of tablets, capsules, or granules, containing suitable excipients such as starch, lactose, white sugar and the like. The inhibitors of aminoglycoside 6'-N-acetyltransferases may be administered orally in the form of solutions which may contain coloring and/or flavoring agents. The inhibitors of aminoglycoside 6'-N-acetyltransferases may also be administered sublingually in the form of tracheas or lozenges in which the active ingredient(s) is/are mixed with sugar or corn syrups, flavoring agents and dyes, and then dehydrated sufficiently to make the mixture suitable for pressing into solid form.

The solid oral compositions may be prepared by conventional methods of blending, filling, tabletting, or the like. Repeated blending operations may be used to distribute the active agent(s) (i.e. inhibitors of aminoglycoside 6'-N-acetyltransferases) throughout those compositions employing large quantities of fillers. Such operations are, of course, conventional in the art. The tablets may be coated according to methods well known in normal pharmaceutical practice, in particular with an enteric coating.

Oral liquid preparations may be in the form of emulsions, syrups, or elixirs, or may be presented as a dry product for reconstitution with water or other suitable vehicle before use. Such liquid preparations may or may not contain conventional additives. Non limiting examples of conventional additives include suspending agents such as sorbitol, syrup, methyl cellulose, gelatin, hydroxyethylcellulose, carboxymethylcellulose, aluminum stearate gel, or hydrogenated edible fats; emulsifying agents such as sorbitan monooleate or acaci; non-aqueous vehicles (which may include edible oils), such as almond oil, fractionated coconut oil, oily esters selected from the group consisting of glycerine, propylene glycol, ethylene glycol, and ethyl alcohol; preservatives such as for instance methyl para-hydroxybenzoate, ethyl para-hydroxybenzoate, n-propyl parahydroxybenzoate, or n-butyl parahydroxybenzoate or sorbic acid; and, if desired, conventional flavoring or coloring agents.

For parenteral administration, fluid unit dosage forms may be prepared by utilizing the inhibitor(s) of aminoglycoside 6'-N-acetyltransferases and a sterile vehicle, and, depending on the concentration employed, the inhibitor(s) of aminoglycoside 6'-N-acetyltransferases may be either suspended or dissolved in the vehicle. Once in solution, the inhibitor(s) of aminoglycoside 6'-N-acetyltransferases may be injected and filter sterilized before filling a suitable vial or ampoule followed by subsequently sealing the carrier or storage package. Adjuvants, such as a local anesthetic, a preservative or a buffering agent, may be dissolved in the vehicle prior to use. Stability of the pharmaceutical composition may be enhanced by freezing the composition after filling the vial and removing the water under vacuum, (e.g., freeze drying). Parenteral suspensions may be prepared in substantially the same manner, except that the inhibitor(s) of aminoglycoside 6'-N-acetyltransferases should be suspended in the vehicle rather than being dissolved, and, further, sterilization is not achievable by filtration. The inhibitor(s) of aminoglycoside 6'-N-acetyltransferases may be sterilized, however, by exposing it to ethylene oxide before suspending it in the sterile vehicle. A surfactant or wetting solution may be advantageously included in the composition to facilitate uniform distribution of the inhibitor(s) of aminoglycoside 6'-N-acetyltransferases.

The pharmaceutical compositions of the present invention comprise a pharmaceutically effective amount of an inhibitor(s) of aminoglycoside 6'-N-acetyltransferases as described herein and one or more pharmaceutically acceptable carriers, excipients and/or diluents. In an embodiment of the present invention, the pharmaceutical compositions contain from about 0.1% to about 99% by weight of an inhibitor(s) of aminoglycoside 6'-N-acetyltransferases as disclosed herein. In a further embodiment of the present invention, the pharmaceutical compositions contain from about 10% to about 60% by weight of an inhibitor(s) of aminoglycoside 6'-N-acetyltransferases as disclosed herein, depending on which method of administration is employed. Physicians will determine the most-suitable dosage of the present therapeutic agents (i.e. inhibitors of aminoglycoside 6'-N-acetyltransferases). Dosages may vary with the mode of administration and the particular inhibitor of aminoglycoside 6'-N-acetyltransferases chosen. In addition, the dosage may vary with the particular patient under treatment. The dosage of the inhibitor of aminoglycoside 6'-N-acetyltransferases used in the treatment may vary, depending on the degree of bacterial resistance, the weight of the patient, the relative efficacy of the compound and the judgment of the treating physician.

The aminoglycoside 6'-N-acetyltransferases AAC(6')-Ii and AAC(6')-ly are important enzymes involved in causing resistance to aminoglycoside antibiotics. For the purposes of the present invention, AAC(6')-Ii and AAC(6')ly were selected because structural and mechanistic information is available for these isoforms and because they are chromosomally encoded in *Enterococcus faecium* and *Salmonella enterica* which are one of the leading causes of hospital-acquired infections (Murray, 1990). However, it is to be understood that any of the other known aminoglycoside 6'-N-acetyltransferases [AAC(6')s] are also included for the purposes of the present invention.

Studies by Wright and coworkers suggest that catalysis by AAC(6')-Ii occurs via an ordered bi-bi mechanism (Draker and Wright, 2004; Draker et al., 2003). The proposed steps include: 1) binding of the cofactor acetyl CoA; 2) binding of the aminoglycoside substrate; 3) attack of the 6'-amino group of the aminoglycoside substrate on the CoA acetyl moiety to form a tetrahedral intermediate (Scheme 1); 4) release of the acetylated product; and 5) release of the CoA free thiol (Draker and Wright, 2004; Draker et al., 2003). Mechanistic studies of AAC(6')ly from *Salmonella enterica* by Blanchard et al. suggest that this isoform also proceeds via a tetrahedral intermediate but in a random substrate binding order.

The present invention relates to inhibitors of aminoglycoside 6'-N-acetyltransferases as well as to their synthesis. A generic example of an inhibitor as contemplated by the present invention is illustrated in Scheme 1. The inhibitors of aminoglycoside 6'-N-acetyltransferases were designed to mimic the tetrahedral intermediate (transition state) and inhibit AAC(6')s. Furthermore, the inhibitors of the present invention allow for the study of the catalytic mechanism leading to aminoglycoside resistance. Moreover, the inhibitors of the present invention allow for further refinement of the substrate binding pocket of AAC(6')-Ii and AAC(6')ly

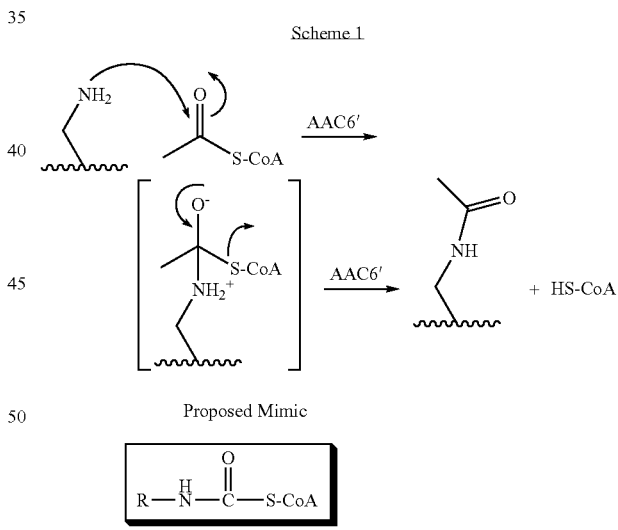

A large number of mono-substituted 4,5- or 4,6-linked aminoglycosides are substrates for AAC(6')s, suggesting a highly flexible binding site (Wright and Ladak, 1997; Boehr et al., 2004; Culebras and Martinez, 1999; Magnet et al., 2001; Magnet et al., 2003; Li et al., 2003). AAC(6')-Ii has also been shown to acetylate poly-L-lysine, histones and other proteins at specific ε-amino groups of lysine residues (Wybenga-Groot et al., 1999). Assuming that lysine and its derivatives are the smallest substrates for AAC(6')-Ii, two lysine-CoA bi-substrate analogs were prepared as shown below in Scheme 2.

Scheme 2

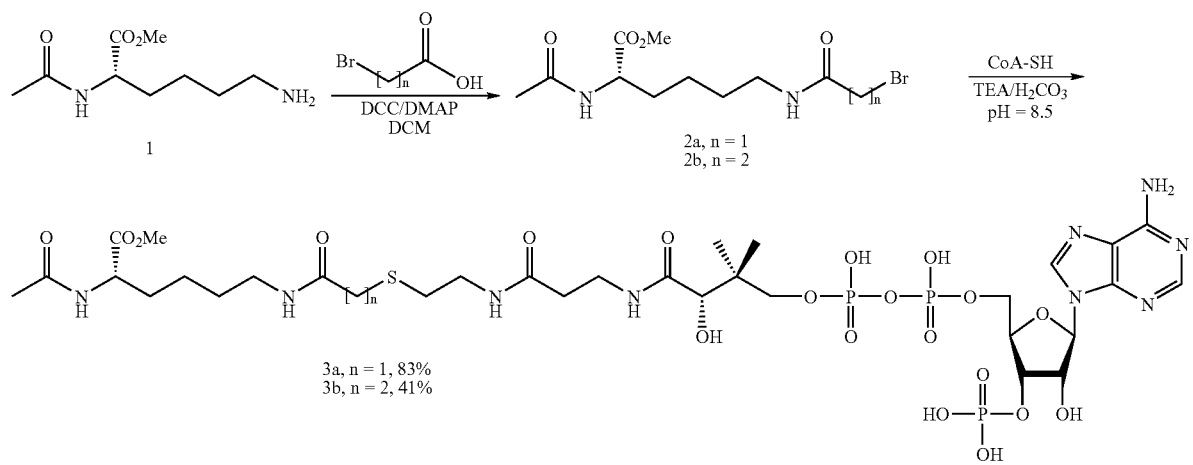

Protected lysine 1 was coupled to bromoacetic acid or 1-bromopropionic acid using DCC, affording 2a and 2b respectively. Compounds 2a and 2b were next reacted with CoA in triethylammonium carbonate buffer (pH=8.1-8.5) (Zheng and Cole, 2003) to yield 3a and 3b respectively. Preparation of the conjugate having an acetyl linker (3a) proceeded in high yield (83%), the reaction being complete within one hour. On the other hand, the preparation of the conjugate having a propanoyl linker (3b) proceeded in a significantly reduced yield (41%). The yield could not be improved by increasing reaction times. A possible explanation for the reduced yield can be found in the higher electrophilicity of bromide 2a due to its proximity to the carboxyl group. Inhibition assays using 3a and 3b revealed moderate inhibition of AAC(6')-Ii with an inhibition constant ($K_i$) of 130 μM and 30 μM respectively. Lysine is a poor substrate for this enzyme [AAC(6')-Ii] and the present results suggest that covalent attachment to CoA does not improve its affinity for the enzyme (acetyl CoA Michaelis-Menten constant ($K_m$) =23.5 μM) (Wright and Ladak, 1997; Boehr et al., 2004; Culebras and Martinez, 1999; Magnet et al., 2001; Magnet et al., 2003; Li et al., 2003).

AAC(6')-Ii is a member of the GCN5-related N-acetyltransferase (GNAT) superfamily (Wybenga-Groot et al., 1999). These enzymes have a highly conserved structure around the acetyl CoA binding pocket, whereas residues around the second binding site have poorly conserved sequences, explaining the diversity of substrates ranging from histones to serotonin to aminoglycoside antibiotics (Marmorstein, 2001). The moderate competitive inhibition observed with 3a and 3b implies that they are not behaving as "true" conjugates, but merely as extended acetyl CoA derivatives having at best an affinity equal to acetyl CoA (i.e., they only compete with acetyl CoA for the first substrate binding, which is not likely the determining step).

Since neamine appears to be the minimal aminoglycoside substrate of AAC6'-Ii (Wright and Ladak, 1997; Boehr et al., 2004; Culebras and Martinez, 1999; Magnet et al., 2001; Magnet et al., 2003; Li et al., 2003), a neamine-CoA conjugate was prepared as illustrated in Scheme 3.

Scheme 3

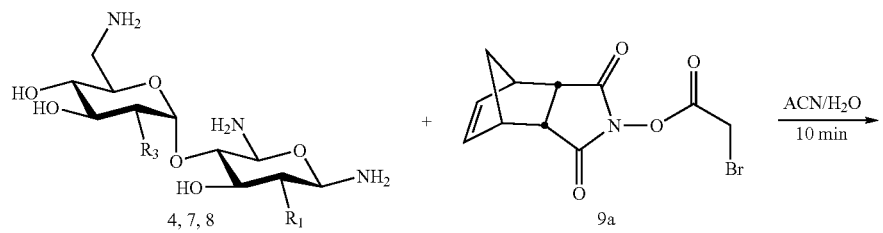

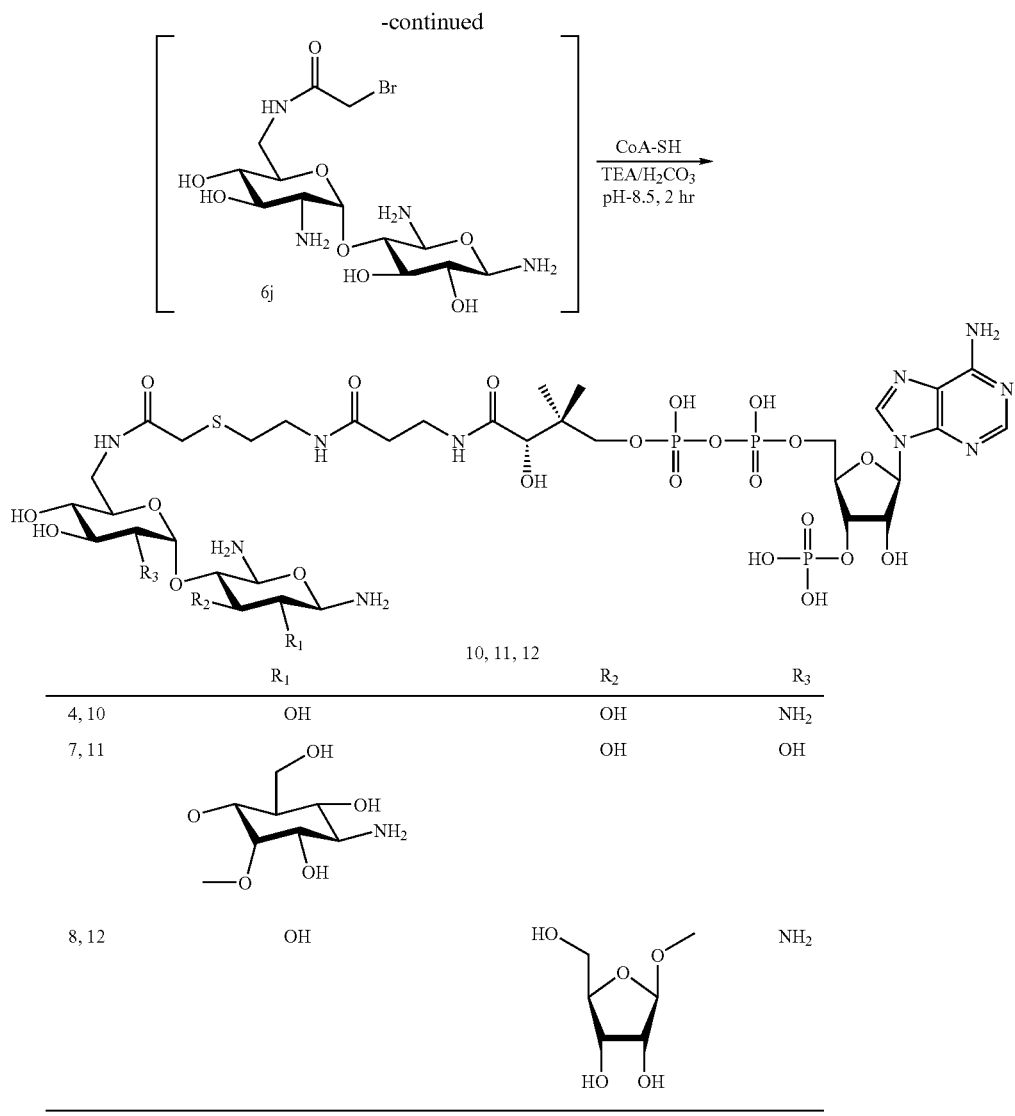

In order to selectively link CoA to the 6'-NH$_2$ of neamine, the other three NH$_2$ groups must be masked (protected). This is usually achieved using an orthogonal protection strategy. The 6'-NH$_2$ is first protected, followed by the orthogonal protection of the remaining three amino groups. Following deprotection of the 6'-NH$_2$, the coupling reaction is carried out followed by deprotection of the other three remaining amino groups. A minimum of five steps are required to link CoA to the 6'-NH$_2$ of neamine, using this conventional approach.

The regioselective protection of the 6'-NH$_2$ group is well documented in the litterature (Schepdael et al., Georgiadis and Constantinou-Kohotou, 1991). The use of transition metals to form a complex with the β-amino alcohol functionality of aminoglycosides (Hanessian and Patil, 1978) has been reported for regioselectively protecting the 6'-NH$_2$ group. This, however, has often proven to be ineffective (Nunns et al., 1999). Primary amines attached to a primary carbon are sterically less hindered than those on a secondary carbon, but are often less nucleophilic (Boto and Coxon, 1983). This suggests that a bulky acylating agent may selectively acylate the 6'-NH$_2$ group. N-hydroxysuccinyl esters have been widely used to transfer an acyl group to the ε-NH$_2$ of lysine residues in proteins. Since N-hydroxy dicarboximide is an excellent leaving group, N-hydroxysuccinyl esters transfer acyl groups to amines rapidly and efficiently (Hermanson, 1995). Endo-N-(tert-butoxycarbonyloxy)-5-norbornene-2,3-dicarboximide (Boc-NBD) has been used to regioselectively introduce the tert-butoxycarbonyl (BOC) protective group at the 6'-NH$_2$ of aminoglycosides (Grapsas et al., 1994). Even though this protection strategy has been successfully applied to the synthesis of some aminoglycoside derivatives (Grapsas et al., 1994), it has also failed in other cases (Nunns et al., 1999).

Instead of selectively protecting all of the amino groups except the 6'-NH$_2$ of aminoglycosides, the use of endo-N-hydroxyl-5-norbornene-2,3-dicarboximide (NBD) esters for the selective derivatization of the 6'-NH$_2$ of aminoglycosides was investigated. In a mixture of acetonitrile/H$_2$O, THF/H$_2$O or acetone/H$_2$O, all acyl transfer reactions tested were highly efficient and complete within 30 minutes (Scheme 4). Extensive 1-D and 2-D NMR analyses confirmed the regioselectivity for the 6'-NH$_2$ group. Interestingly, the regioselectivity observed with different NBD esters was also dependent on the bulkiness of the acyl group transferred (Scheme 4). The bulkier the R-group the better the selectivity, until the donor becomes too sterically hindered, e.g., 2-methyl-benzoyl or 2,6-dichloro-benzoyl (acylating reagents 5h and 5i respectively). This reaction was also tested with more complex aminoglycosides such as kanamycin A and ribostamycin and showed excellent selectivity for 6'-NH$_2$ position. On the other hand, neomycin B, which has two primary amino groups on primary carbons, yielded the doubly acylated product.

Scheme 4

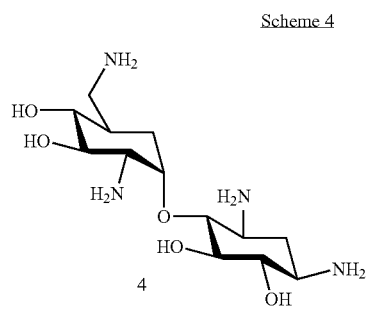

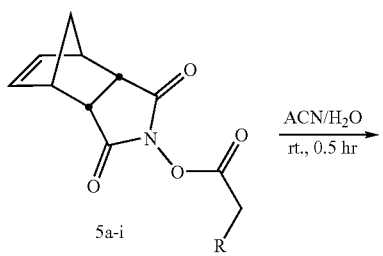

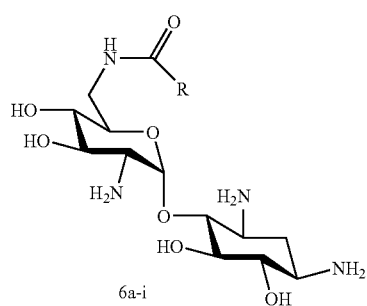

| | R | Y.% |
|---|---|---|
| a | CH$_3$ | 60[a] |
| b | n-C$_3$H$_7$ | 70[b] |
| c | n-C$_{11}$H$_{23}$ | 70[b] |
| d | phenyl | 80[a] |
| e | benzyl | 75[a] |
| f | naphthylmethyl | 85[a] |
| g | 2-chlorophenyl | 90[b] |
| h | 2-methylphenyl | N.R.[c] |
| i | 2,6-dichlorophenyl | N.R.[c] |

[a] recovered yield
[b] estimated by HPLC
[c] no reaction

As illustrated in Scheme 3, this novel regioselective acylation reaction was used to transfer a bromoacetyl group onto the 6'-NH$_2$ group of aminoglycosides 4, 7 and 8. When followed by nucleophilic substitution using CoA free thiol, conjugates are provided in merely two steps, as opposed to the previously reported six steps using an orthogonal protection route (Sainlos et al., 2003). Upon reaction between neamine (4) and NBD ester 9a, the bromide intermediate 6j was formed within 10 minutes, but could not be isolated because of rapid decomposition. To avoid this problem, the acylation and subsequent nucleophilic substitution reactions were carried in one-pot. Thus after 10 minutes of mixing neamine (4) with the acylating agent 9a, the mixture was transferred to a solution of CoA free thiol. Surprisingly, this procedure proved to be efficient, affording compound 10 in 83% yield.

Using a similar procedure, the kanamycin-CoA conjugate (11) and the ribostamycin-CoA conjugate (12) were successfully prepared in yields of 72% and 67% respectively (Scheme 3). The conjugates (10, 11 and 12) displayed a 500-fold enhanced inhibition of AAC(6')-Ii as compared to lysine-CoA conjugates (3a and 3b) (Table 1). Unexpectedly, conjugates 10, 11 and 12 displayed competitive inhibition versus acetylCoA. On the other hand, the fact that conjugates 10, 11 and 12 show comparable inhibition implies that the binding pocket for the aminoglycoside component is highly promiscuous. In addition, this observation suggests that neamine is the minimal aminoglycoside required in the design of AAC(6')-Ii conjugate inhibitors.

TABLE 1

Kinetic data for the inhibition assays of AAC(6')-Ii

|    | $V_m$ (µM/sec) | $K_m$ (µM) | $K_i$ (µM) |
|----|----------------|------------|------------|
| 3a |                |            | ≧130 |
| 3b |                |            | ≧30 |
| 10 | 0.15 ± 0.01 | 6.5 ± 0.43 | 0.076 ± 0.025 |
| 11 | 0.17 ± 0.04 | 6.1 ± 1.4 | 0.111 ± 0.028 |
| 12 | 0.14 ± 0.04 | 15.9 ± 4.5 | 0.119 ± 0.014 |

In order to study the effect of the length of the linker ("Y") between the two substrates (i.e. aminoglycoside and CoA) on the inhibition, neamine-CoA bi-substrate analogs with longer linkers were prepared. Unfortunately, the conditions used to synthesize bi-substrate analogs 10-12 yielded mixtures when applied to the synthesis of analogs with longer linkers (Scheme 5). Some of the side products observed include the addition product of CoA onto the double bond of endo-N-hydroxy-5-norbornene-2,3-dicarboximide; the N-alkylation product of the bromide intermediate by a second neamine molecule; the triethylammonium adduct and its elimination product. Converting bromide 9b to an iodide did not overcome the problem.

Triethylamine (TEA) is nucleophilic and may attack the bromide. The high concentrations of TEA used may have exacerbated the observed side reactions. Moreover, TEA does not fully deprotonate thiols and thus under the conditions used the thiol of CoA may not have competed well with the amino groups of another neamine molecule in attacking the bromide, and may have instead added to the softer electrophile C=C. This suggests that the reaction could be optimized by varying the nature of the base. To this end, the model reaction between N-acetylcysteine (to mimic CoA) and neamine was used to explore conditions favorable to chemoselective S-alkylation over N-alkylation in aqueous media. Most reported procedures for regioselective alkylation by a thiol group (Moiseev et al., 2003) or cysteine (Perrey and Uckun, 2001; Yang et al., 1991) were not compatible with the presently used reagents and a detailed investigation was required. Thus, an array of bases was examined as illustrated in Scheme 6. Even though in low yield, only DIPEA (Hunig's base) yielded the expected product 13. The reaction was further optimized by addition of dithiothreitol (DTT, 0.03% w/v) and by increasing the proportion of base (20 eq. DIPEA). After addition of the CoA solution, the reaction was sonicated. Under these optimized conditions the reaction proceeded rapidly and efficiently.

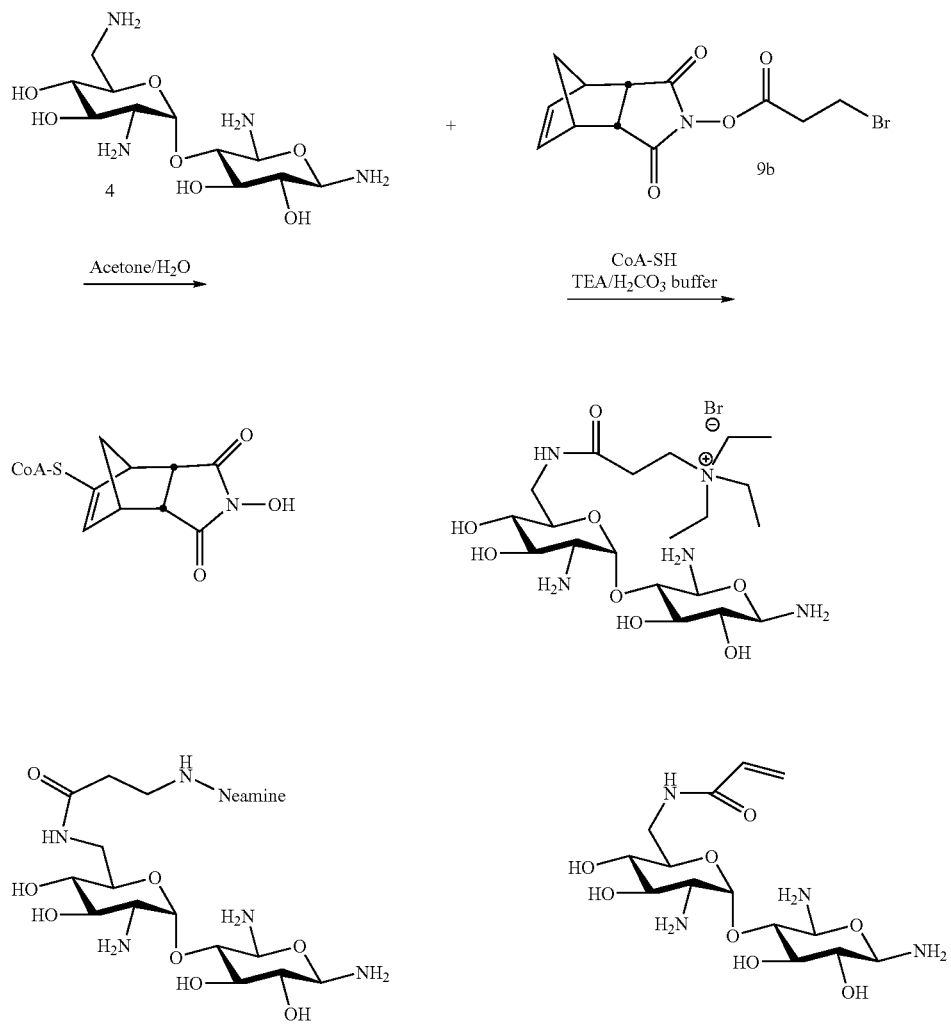

Scheme 6

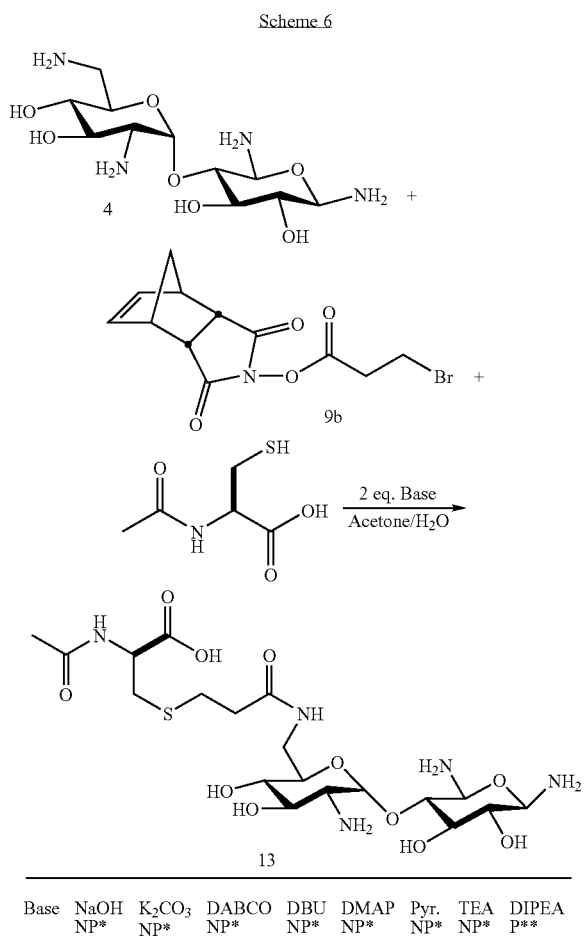

| Base | NaOH | K₂CO₃ | DABCO | DBU | DMAP | Pyr. | TEA | DIPEA |
|------|------|-------|-------|-----|------|------|-----|-------|
|      | NP*  | NP*   | NP*   | NP* | NP*  | NP*  | NP* | P**   |

**P: product was detected;
*NP: no product was detected

Under these conditions, conjugates 10b, 10c and 10d were prepared in very high (10b, 91% and 10d, 93%) to moderate (10c, 52%) yields (Scheme 7). Neamine-CoA conjugates 10a, 10b and 10c were found to be potent competitive inhibitors of AAC(6')-Ii with Ki values in the submicromolar range (Table 2). Conjugate 10b showed the highest inhibition among all the inhibitors. Moreover, neamine-CoA conjugates 10a, 10b, 10c and 10d were also found to inhibit AAC(6')-Iy with near submicromolar Ki values (Table 2).

It has been previously suggested that the main role of AAC6'-Ii in the N-acetyl transfer was to bring the nucleophilic 6'-NH$_2$ of the aminoglycoside in proximity to the electrophilic thioester of acetyl CoA (Zheng and Cole, 2003). The crystal structures reported for AAC(6')-Ii provide no evidence for stabilization of the tetrahedral intermediate (Wybenga-Groot et al., 1999; Burk et al., 2003). The K$_i$s calculated for the aminoglycoside-CoA conjugates are several orders of magnitude lower than the K$_m$ values of the aminoglycoside substrates (6-36 μM) and that of acetyl CoA (23.5 μM) for AAC(6')-Ii. Assuming that the conjugates of the present invention are good mimics of the tetrahedral reaction intermediate, the present results suggest that the enzyme not only acts by a proximity effect but that it also participates in the stabilization of the intermediate by binding it more tightly than the starting materials. The crystal structures of AAC(6')-Ii, complexed to either AcCoA (Wybenga-Groot et al., 1999) or CoA (Burk et al., 2003), have been solved. The reported structure of AAC(6')-Ii has provided important information about the general fold and the binding site of CoA and acetyl CoA (Wybenga-Groot et al., 1999; Burk et al., 2003).

TABLE 2

Kinetic data for the inhibition assays of AAC(6')-Ii and AAC(6')-Iy

| Inhibtor | AAC(6')-Ii [K$_i$; (μM)] | AAC(6')-Iy [K$_i$; (μM)] |
|----------|--------------------------|--------------------------|
| 10a      | 0.076 ± 0.025            | 2.76 ± 0.4               |
| 10b      | 0.043 ± 0.023            | 1.89 ± 0.3               |
| 10c      | 0.161 ± 0.098            | 2.1 ± 0.3                |
| 10d      | 7.99 ± 2.66              | 1.9 ± 0.3                |
| 11       | 0.111 ± 0.028            | 2.3 ± 0.5                |
| 12       | 0.119 ± 0.014            | 1.1 ± 0.1                |

Scheme 7

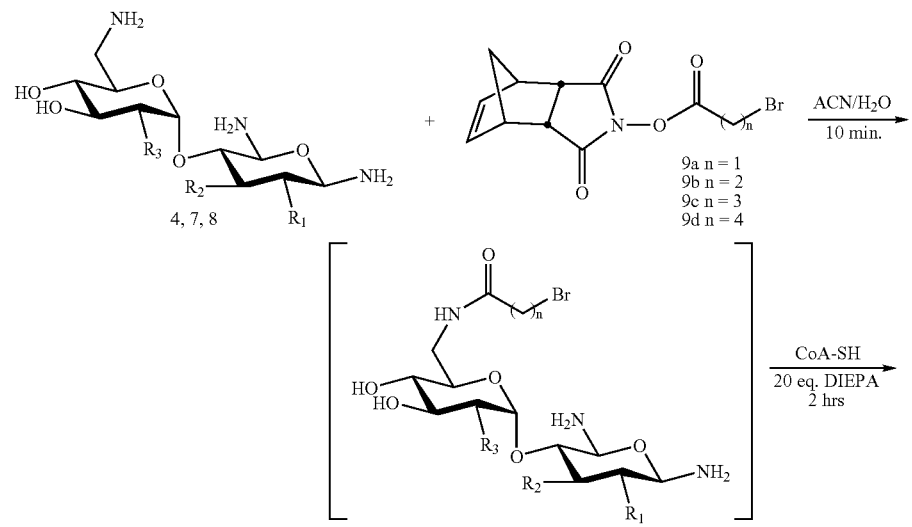

-continued
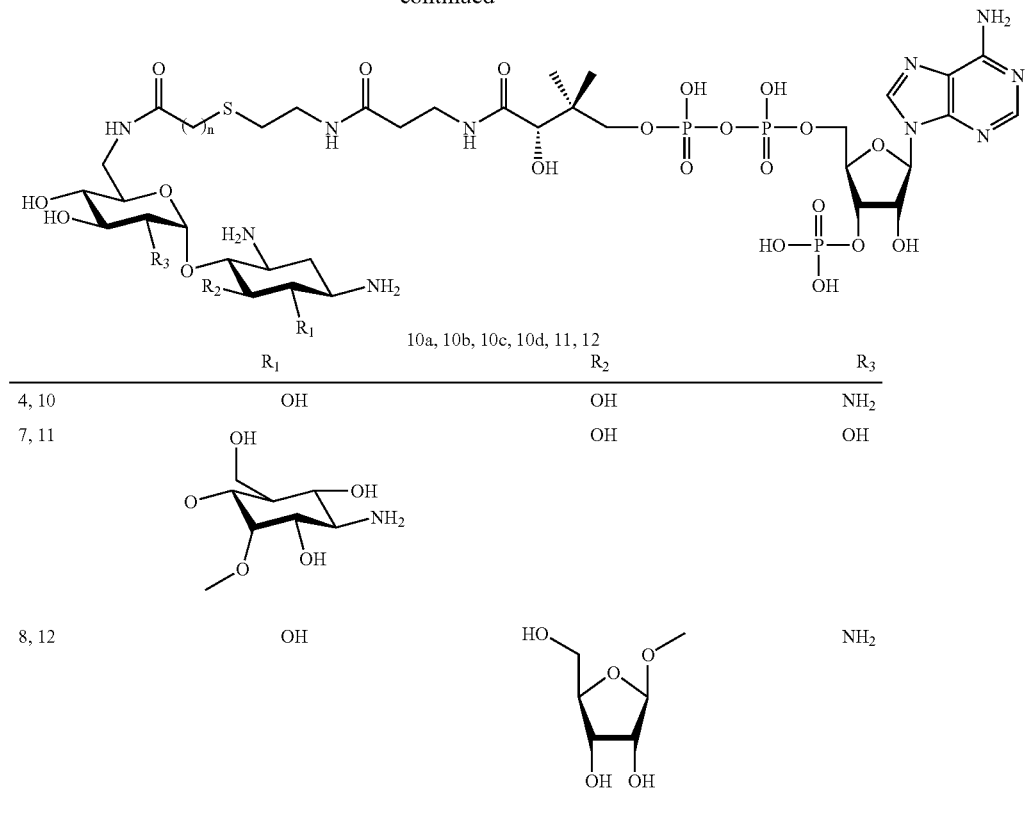
| | $R_1$ | $R_2$ | $R_3$ |
|---|---|---|---|
| 4, 10 | OH | OH | $NH_2$ |
| 7, 11 | OH | OH | OH |
| | (structure shown) | | |
| 8, 12 | OH | (structure shown) | $NH_2$ |
Additional inhibitors of aminoglycoside 6'-N-acetyltransferases are illustrated hereinbelow in Scheme 8.
Scheme 8
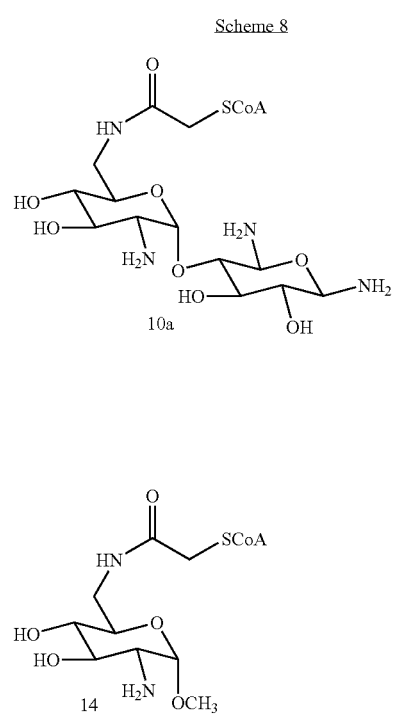
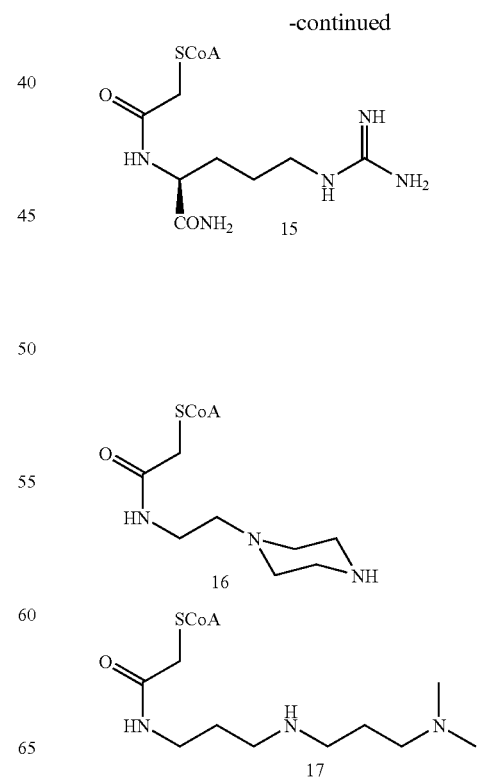

-continued

| Inhibitor | AAC(6')-Ii [$K_i$ (μM)] |
|---|---|
| 10a | 0.076 ± 0.025 |
| 14 | 49 ± 26 |
| 15 | 28 ± 3 |
| 16 | 8 ± 1 |
| 17 | 10 ± 5 |

The inhibition constants as observed in Scheme 8 corroborate previously observed results from which it appeared that neamine is the minimal aminoglycoside required in the design of AAC(6')-Ii conjugate inhibitors. Additional neamine-based aminoglycoside conjugates as contemplated by the present invention are illustrated hereinbelow in Scheme 9.

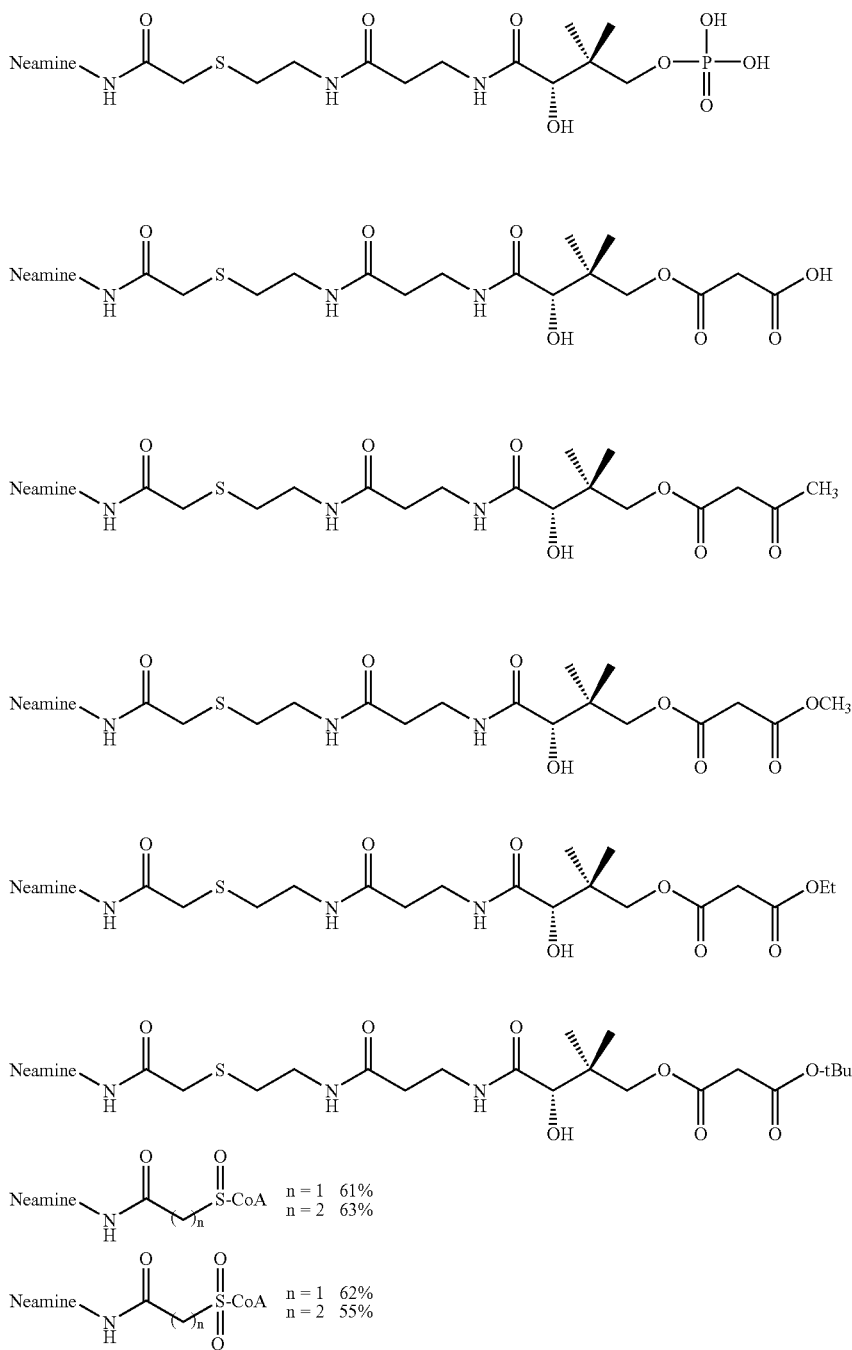

The preparation of selective examples of neamine-based aminoglycoside 6'-N-acetyltransferase inhibitors is illustrated hereinbelow in Schemes 10, 11, and 12.
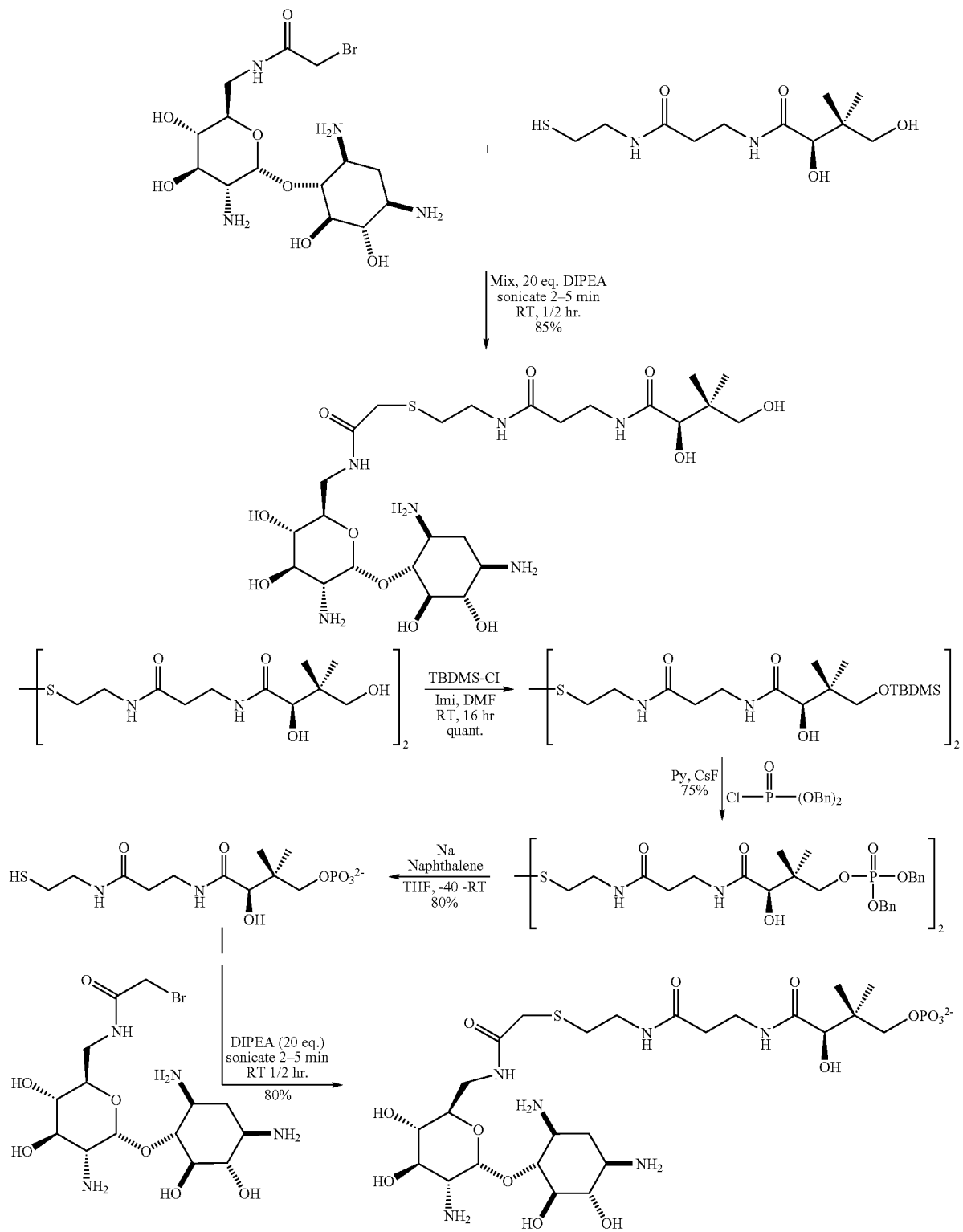
Scheme 10

Scheme 11
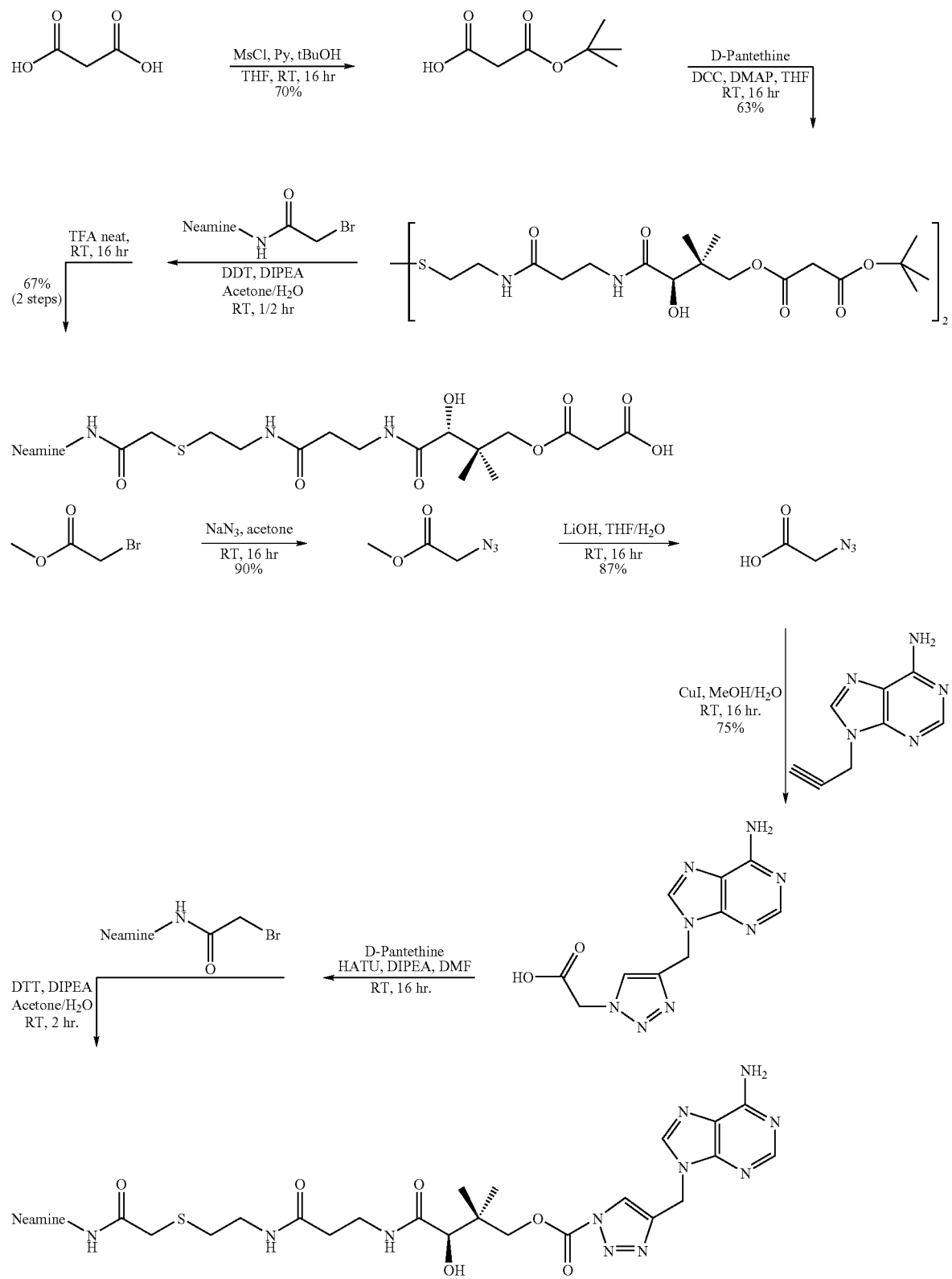

Scheme 12
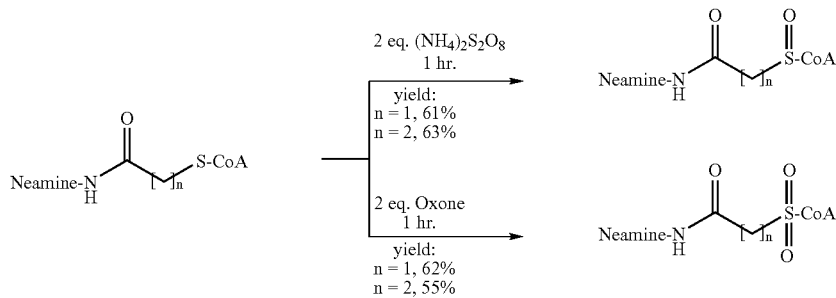
The preparation of aminoglycoside 6'-N-acetyltransferase inhibitors 14, 15, 16 and 17 is illustrated hereinbelow in Schemes 13 and 14.
Scheme 13
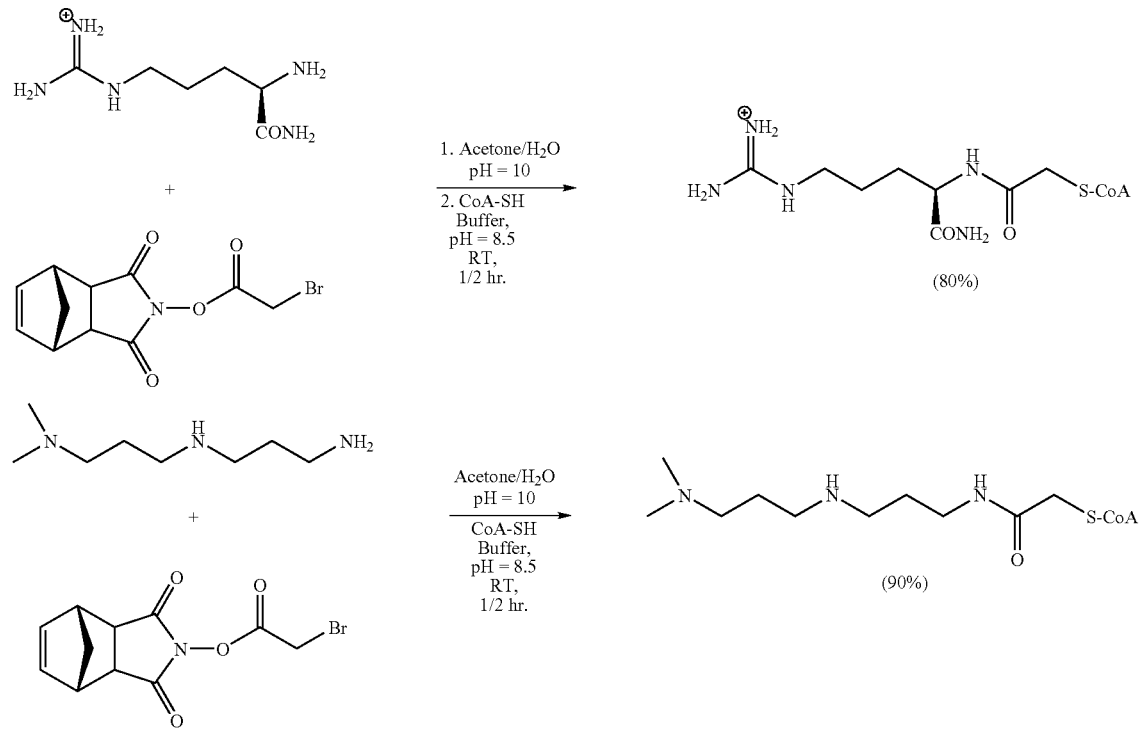
Scheme 14
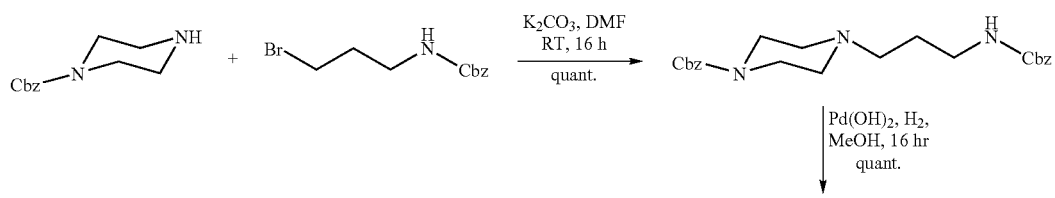

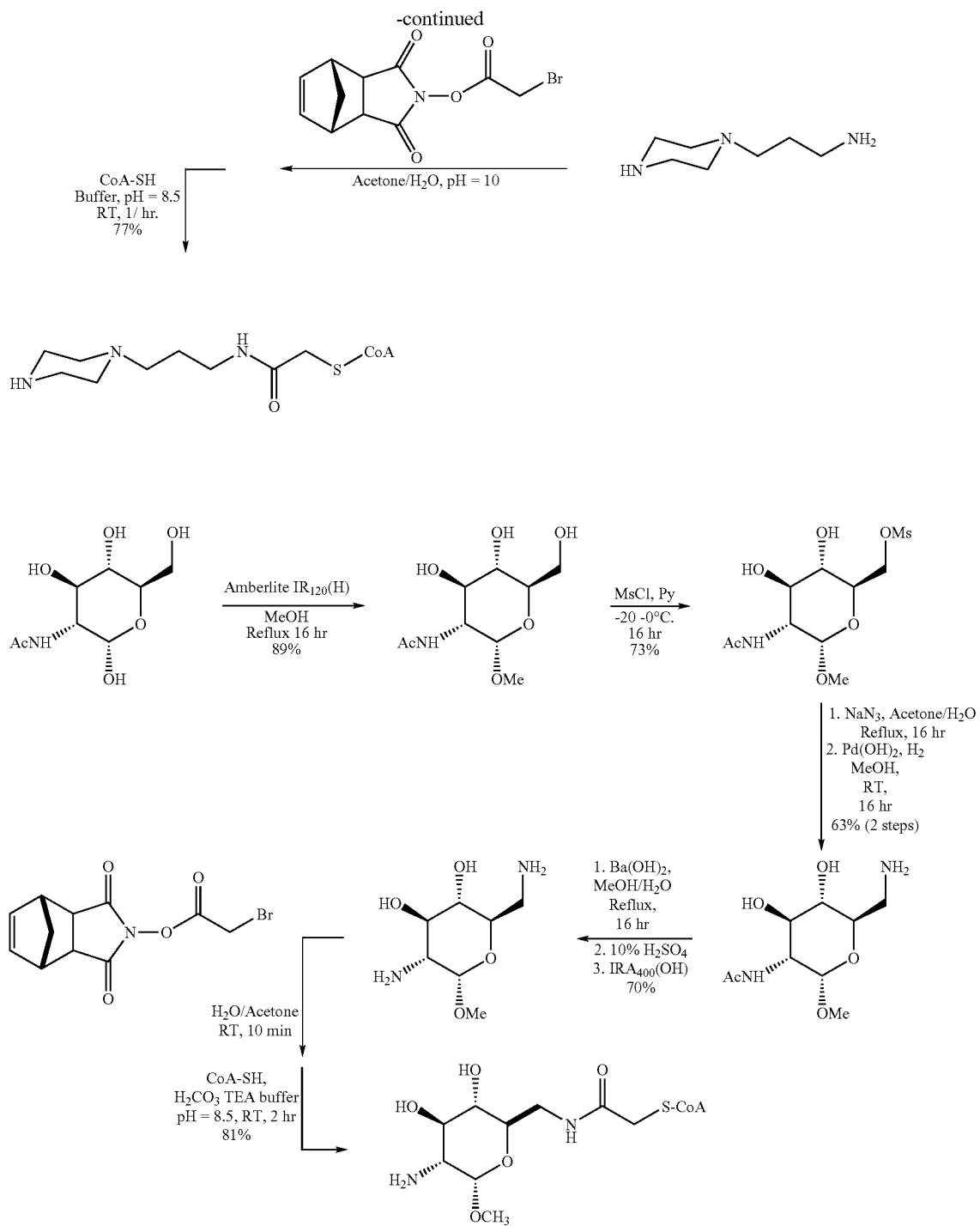

The synthesis and characterization of non-limiting representative examples of inhibitors of aminoglycoside 6'-N-acetyltransferases as contemplated by present invention, is further detailed in the following sections.

EXPERIMENTAL

General procedures: Unless mentioned otherwise, all reactions were performed at room temperature under an atmosphere of argon and in flame-dried flasks capped with rubber septa. Synthesis of 2a-b, 5a-i and 9a-d were monitored by TLC on EM silica gel 60 F254 plates and visualized by UV light (254 nm) or potassium permanganate spray. Preparation of 3a-b, 6a, 6d, 6e, 6f, 10a-d, 11 and 12 were monitored by MS. Compounds 6b, 6c, and 6g were not isolated.

Compounds 3a-b, 6a, 6d-f, 10a-d, 11 and 12 were purified by reversed-phase HPLC using an Agilent Zorbax SB-CN column (4.6×250 mm, 5µ) on an Agilent 1100 system with diode array UV detector. Samples were eluted at a flow rate of 3 ml/min, using the linear gradients shown in Table 3.

TABLE 3

| Gradient profile for HPLC purification | | |
|---|---|---|
| Time (min) | % A (0.05% TFA in $H_2O$) | % B (0.04% TFA in ACN) |
| 0 | 98 | 2 |
| 20 | 60 | 40 |
| 25 | 0 | 100 |
| 28 | 0 | 100 |
| 35 | 98 | 2 |

Instrumentation: Melting points were not corrected. HRMS of compounds 3a-b, 10a-d, 11 and 12 were analyzed by direct infusion electrospray ionization from a 90:10 solution (methanol:50 mM aqueous ammonium hydroxide) at 2 μL/min using an IonSpec 7 Tesla FTICR instrument at a resolving power of approximately 80,000. Other HRMS samples were analyzed using a Kratos MS 25RFA mass spectrometer at a source temperature of 200° C. and 70 eV. LRMS was performed using a Finnigan LCQDUO mass spectrometer with either ESI or APCI without fragmentation. Routine $^1H$ and $^{13}C$ NMR spectra were recorded using Varian mercury 400 or 300 or Unity 500 spectrometers. The chemical shifts (δ) were reported in parts per million (ppm) relative to the internal standard TMS (0 ppm). The peak patterns are indicated as follows: s: singlet; d: doublet; dd: doublet of doublet; t: triplet; tt: triplet of triplet; dt: doublet of triplet; ddd: doublet of doublet of doublet; td: triplet of doublet; m: multiplet; q: quartet; br s: broad singlet, etc. All $^1H$ NMR and correlation spectra including COSY, HMBC and HSQC of aminoglycoside coenzyme conjugates (i.e. inhibitors of aminoglycoside 6'-N-acetyltransferases) and aminoglycosides were recorded with solutions of pD=4 unless otherwise stated. $^1H$ and $^{13}C$ NMR assignments were confirmed by HSQC, HMQC, and HMBC.

$^1H$ and $^{13}C$ NMR Assignment of Coenzyme A $^1H$ NMR ($D_2O$, 500 MHz, pD=6, presaturated) δ 8.44 (s, H8), 8.24 (s, H2), 6.02 (d, J=5.5 Hz, H1'), 4.75 (m, H2', H4'), 4.41 (br s, H3'), 4.08 (m, H10), 3.83 (s, H12), 3.64 (dd, J=9.2, 4.8 Hz, H5'), 3.38 (dd, J=9.2, 4.8 Hz, H5'), 3.28 (t, J=7.2 Hz, H15), 3.13 (t, J=7.2 Hz, H19), 2.41 (t, J=7.2 Hz, H20), 2.28 (t, J=7.2 Hz, H16), 0.71 (s, H21), 0.58 (s, H1). $^{13}C$ NMR ($D_2O$, 125 MHz) δ 174.7 (C13), 174.0 (C17), 154.0 (C6), 150.7 (C2), 149.2 (C4), 140.6 (C8), 118.9 (C5), 86.7 (C1'), 83.7 (C3'), 74.3 (C12), 74.3 (C4'), 73.9 (C2'), 72.0 (C5'), 65.4 (C1), 42.5 (C19), 38.6 (C15), 35.7 (C16), 23.3 (C20), 21.1 (C21 or C22), 18.4 (C21 or C22).

$^1H$, $^{13}C$ NMR and HRMS Assignment of Compounds 2a-b

2a: Rf=0.28 (EtOAc/iPrOH, 20/1), yield: 74%. $^1H$ NMR (CDCl$_3$, 400 MHz): δ 6.30 (br s, NH), 6.09 (br s, NH), 4.55 (m, 1H), 3.86 (s, 2H), 3.74 (s, 3H), 3.28 (m, 2H), 2.03 (s, 3H), 1.88 (m, 1H), 1.75 (m, 1H), 1.56 (m, 2H), 1.36 (m, 2H); $^{13}C$ NMR (CDCl$_3$, 1100 MHz), δ 173.0, 170.3, 165.9, 52.9, 52.0, 39.9, 32.3, 29.6, 28.9, 23.6, 22.6; HRMS for $C_{11}H_{19}BrN_2O_4$ (M+H) calculated: 322.05 (100) and 324.05 (97); found: 322.03 (100) and 324.03 (97).

2b: Rf=0.25 (CHCl$_3$/MeOH, 10/1), yield: 55%. $^1H$ NMR (CDCl$_3$, 400 MHz): δ 6.33 (br s, NH), 6.11 (br s, NH), 4.56 (m, 1H), 3.73 (s, 3H), 3.63 (t, J=6.4, 2H), 3.26 (m, 2H), 2.74 (br t, J=6.4 Hz, 2H), 2.04 (s, 3H), 1.81 (m, 1H), 1.70 (m, 1H), 1.55 (m, 2H), 1.38 (m, 2H); $^{13}C$ NMR (CDCl$_3$, 100 MHz): δ 172.5, 170.0, 167.9, 52.2, 51.7, 39.4, 38.7, 32.0, 28.4, 27.7, 23.1, 21.9; HRMS for $C_{12}H_{21}BrN_2O_4$ (M+H) calculated: 336.05 (100) and 338.05 (97); found: 336.03 (100) and 338.03 (100).

$^1H$, $^{13}C$ NMR, HRMS(3a) and MS(3b) Assignment of Compounds 3a-b

3a: Yield: 83%. $^1H$ NMR (D$_2$O, 400 MHz, presaturated): δ 8.31 (s, 1H), 8.13 (s, 1H), 6.05 (d, J=7.2 Hz, 1H), 4.46 (s, 1H), 4.20 (dd, J=8.8, 3.6 Hz, 1H), 4.13 (s, 2H), 3.91 (s, 1H), 3.68 (br d, J=9.2 Hz, 1H), 3.64 (s, 3H), 3.44 (br d, J=9.2 Hz, 1H), 3.35 (t, J=6.4 Hz, 2H), 3.25 (t, J=6.4 Hz, 2H), 3.14 (s, 2H), 3.08 (t, J=6.4 Hz, 2H), 2.56 (t, J=6.4 Hz, 2H), 2.35 (t, J=6.4 Hz, 2H), 1.93 (s, 3H), 1.81 (m, 1H), 1.61 (m, 1H), 1.40 (m, 2H), 1.24 (m, 2H), 0.76 (s, 3H), 0.63 (s, 3H); $^{13}C$ NMR (D$_2$O, 125 MHz, from HMQC and HMBC): δ 174.7, 174.4, 174.3, 174.2, 174.0, 154.1, 150.8, 149.3, 140.5, 119.2, 95.4, 94.2, 86.8, 84.0, 74.2, 74.0, 73.8, 72.1, 71.9, 68.0, 67.6, 65.7, 53.5, 39.1, 38.2, 35.8, 35.4, 34.6, 31.4, 21.3, 20.4, 18.0; HRMS for $C_{32}H_{54}N_9O_2P_3S$ (M+H) calculated: 1010.24; found: 1010.10.

3b: Yield: 41%. $^1H$ NMR (D$_2$O, 400 MHz, presaturated): δ 8.58 (s, 1H), 8.33 (s, 1H), 6.12 (d, J=7.2 Hz, 1H), 4.65 (s, 1H), 4.20 (dd, J=8.8, 3.6 Hz, 1H), 4.15 (s, 2H), 3.93 (s, 1H), 3.74 (d, J=9.2 Hz, 1H), 3.63 (s, 3H), 3.51 (d, J=9.2 Hz, 1H), 3.37 (t, J=6.4 Hz, 2H), 3.25 (t, J=6.4 Hz, 2H), 3.07 (t, J=6.4 Hz, 2H), 2.69 (t, J=6.4 Hz, 2H), 2.56 (t, J=6.4 Hz, 2H), 2.37 (m, 4H), 1.91 (s, 3H), 1.72 (m, 1H), 1.62 (m, 1H), 1.40 (p, J=7.2 Hz, 2H), 1.26 (m, 2H), 0.84 (s, 3H), 0.72 (s, 3H); $^{13}C$ NMR (D$_2$O, 100 MHz, from HMQC and HMBC): δ 174.7, 174.4, 174.3, 174.2, 174.0, 154.1, 150.8, 149.3, 140.5, 119.2, 96.4, 93.8, 87.0, 83.8, 74.2, 74.0, 73.8, 72.2, 71.8, 68.1, 67.7, 65.6, 54.0, 39.2, 38.2, 35.8, 35.5, 34.5, 31.5, 28.0, 21.2, 20.5, 18.1; MS for $C_{33}H_{56}N_9O_2P_3S$ (M+H) calculated: 1024.26; found: 1024.11.

$^1H$ and $^{13}C$ NMR Assignment for Neamine

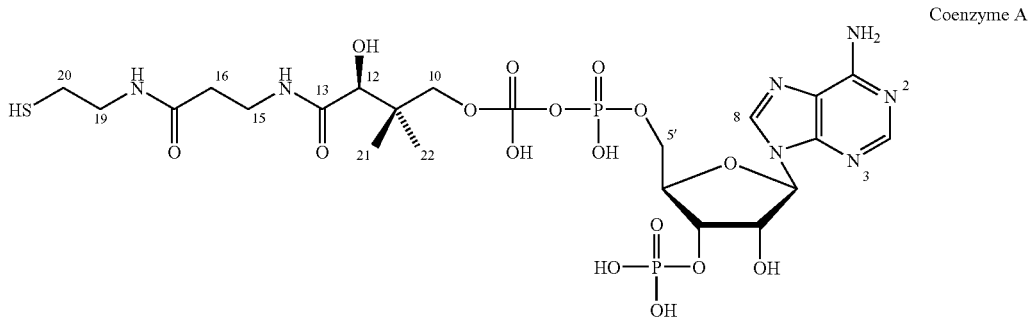

Coenzyme A

The $^1$H NMR spectrum of neamine is strongly depended on the pH/pD value of the solution. Both the free base and the TFA salt of neamine were fully characterized by NMR. In general, the free base produces a cleaner $^1$H NMR spectrum than the TFA salt. Enhanced solvation of the salt form yields much shorter relaxation times and more overlapping chemical shifts. The assignment for the free base neamine, as disclosed herein, is fully consistent with a previous report.

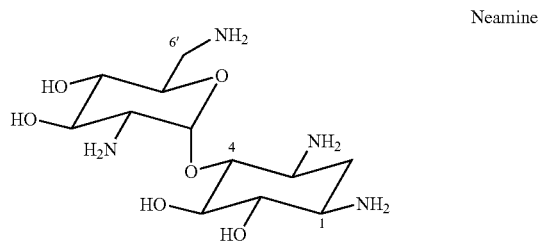

Neamine

Neamine free base: $^1$H NMR (D$_2$O, 400 MHz, presaturated): δ 5.15 (d, J=4.0 Hz, H1'), 3.63 (br t, J~8 Hz, H5'), 3.42 (t, J=9.2 Hz, H3'), 3.36 (m, H5), 3.16 (t, J=9.2 Hz, H4'), 3.13 (t, J=9.2 Hz, H4), 3.00 (t, J=9.6 Hz, H6), 2.89 (dd, J=13.4, 2.6 Hz, H6'), 2.72-2.52 (m, H3, H6', H2', H1), 1.83 (td, J=12.4, 4.0 Hz, H2eq), 1.06 (q, J=12.4 Hz, H2ax). $^{13}$C NMR (D$_2$O, 75 MHz) δ 101.09, (C1'), 87.21 (C4), 77.75 (C6), 76.34 (C5), 73.74 (C3'), 72.79 (C5'), 71.61 (C4'), 55.54 (C2'), 50.18 (C1), 49.63 (C3), 41.60 (C6'), 35.79 (C2).

Neamine HCl salt: $^1$H NMR (D$_2$O, 400 MHz, presaturated): δ 5.85 (d, J=3.5 Hz, H1'), 3.95 (m, H6), 3.90 (m, H4), 3.87 (m, H5), 3.62 (t, J=5.6 Hz, H4'), 3.50 (m, H3') 3.47 (m, H3), 3.45 (m, H5), 3.42 (m, H6'), 3.39 (m, H2'), 3.28 (m, H1), 3.22 (m, H6'), 2.37 (td, J=13.2, 4.0 Hz, H2eq), 1.76 (q, J=13.2 Hz, H2ax). $^{13}$C NMR (D$_2$O, 75 MHz) δ 96.21 (C1'), 77.89 (C5'), 75.37 (C4'), 72.69 (C3'), 70.84 (C5), 69.40 (C6), 68.39 (C4), 53.71 (C2'), 49.90 (C1), 48.62 (C3), 40.32 (C6'), 28.52 (C2).

$^1$H, $^{13}$C NMR and MS assignment of compounds 5a-i

5a: TLC Rf=0.15 in EtOAc/Hex (1/1). Yield: 90%. $^1$H NMR (CDCl$_3$, 400 MHz): δ 6.18 (br s, 2H), 3.45 (br s, 2H), 3.33 (br s, 2H), 2.25 (s, 3H), 1.79 (d, J=8.8 Hz, 1H), 1.54 (d, J=8.8 Hz, 1H); $^{13}$C NMR (CDCl$_3$, 75 MHz) δ 169.5, 135.0, 51.6, 45.1, 43.7, 17.2. MS for C$_{11}$H$_{11}$NO$_4$ (M+H) calculated: 222.07; found: 222.00.

5b: TLC Rf=0.33 in EtOAc/Hex (1/2). Yield: 91%. $^1$H NMR (CDCl$_3$, 400 MHz): δ 6.19 (br s, 2H), 3.45 (br s, 2H), 3.32 (br s, 2H), 2.52 (t, J=7.6 Hz, 2H), 1.77 (m, 3H), 1.54 (d, J=8.8 Hz, 1H), 1.02 (m, 3H); $^{13}$C NMR (CDCl$_3$, 75 MHz): δ 169.9, 134.9, 51.4, 45.1, 43.6, 31.2, 16.3, 13.6; MS for C$_{13}$H$_{15}$NO$_4$ (M+H) calculated: 250.10; found: 250.00.

5c: TLC Rf=0.60 in EtOAc/Hex (1/2). Yield: 90%. $^1$H NMR (CDCl$_3$, 400 MHz): δ 6.18 (br s, 2H), 3.44 (br s, 2H), 3.32 (br s, 2H), 2.53 (t, J=7.6 Hz, 2H), 1.75 (m, 3H), 1.52 (m, 3H), 1.25 (br s, 14H), 0.88 (t, J=6.8 Hz, 3H); $^3$C NMR (CDCl$_3$, 75 MHz): δ 169.9, 134.7, 51.5, 45.4, 43.7, 33.0, 29.6, 29.4, 29.3, 29.1, 29.0, 28.5, 28.5, 23.5, 22.2, 14.1. MS for C$_{21}$H$_{31}$NO$_4$ (M+H) calculated: 362.23; found: 362.20.

5d: TLC Rf=0.65 in EtOAc/Hex (1/1). Yield: 94%. $^1$H NMR (CDCl$_3$, 400 MHz): δ 8.09 (d, J=8.0 Hz, 2H), 7.65 (t, J=8.0 Hz, 1H), 7.48 (t, J=8.0 Hz, 2H), 6.28 (br s, 2H), 3.50 (br s, 2H), 3.40 (br s, 2H), 1.83 (d, J=8.8 Hz, 1H), 1.58 (d, J=8.8 Hz, 1H); $^3$C NMR (CDCl$_3$, 75 MHz): δ 170.2, 134.9, 134.7, 130.7, 130.4, 128.9, 51.7, 45.2, 43.5. MS for C$_{16}$H$_{13}$NO$_4$ (M+H) calculated: 284.08; found: 284.10.

5e: TLC Rf=0.66 in EtOAc/Hex (1/1). Yield: 100%. $^1$H NMR (CDCl$_3$, 400 MHz): δ 7.31 (m, 5H), 6.19 (br s, 2H), 3.87 (s, 2H), 3.44 (br s, 2H), 3.32 (br s, 2H), 1.80 (d, J=8.8 Hz, 1H), 1.58 (d, J=8.8 Hz, 1H); $^{13}$C NMR (CDCl$_3$, 75 MHz): δ 170.0, 135.1, 135.0, 129.5, 129.0, 127.9, 51.5, 45.0, 43.4, 37.2; MS for C$_{17}$H$_{15}$NO$_4$ (M+H) calculated: 298.10; found: 298.00.

5f: TLC Rf=0.55 in EtOAc/Hex (1/1). Yield: 99%. $^1$H NMR (CDCl$_3$, 400 MHz): δ 7.93 (d, J=8.0 Hz, 1H), 7.86 (d, J=8.0 Hz, 1H), 7.82 (d, J=8.0 Hz, 1H), 7.58 (t, J=8.0 Hz, 1H), 7.50 (t, J=8.0 Hz, 1H), 7.45 (m, 2H), 6.15 (br s, 2H), 4.30 (s, 2H), 3.41 (br s, 2H), 3.27 (br s, 2H), 1.74 (br s, 1H), 1.47 (d, J=8.8 Hz, 1H). $^{13}$C NMR (CDCl$_3$, 75 MHz): δ 170.0, 166.4, 150.2, 138.2, 134.9, 127.2, 125.4, 125.0, 124.8, 124.8, 123.8, 122.5, 113.3, 51.2, 44.7, 43.2, 37.8; MS for C$_{21}$H$_{17}$NO$_4$ (M+H) calculated: 348.12; found: 348.10.

5g: TLC Rf=0.53 in EtOAc/Hex (1/1). Yield: 96%. $^1$H NMR (CDCl$_3$, 400 MHz): δ 8.04 (d, J=7.6 Hz, 1H), 7.52 (m, 2H), 7.36 (m, 1H), 6.27 (br s, 2H), 3.50 (br s, 2H), 3.39 (br s, 2H), 1.82 (d, J=8.8 Hz, 1H), 1.57 (d, J=8.8 Hz, 1H); $^{13C}$ NMR (CDCl$_3$, 75 MHz): δ 169.9, 136.5, 134.7, 130.1, 129.0, 127.5, 126.7, 51.2, 44.4, 43.1; MS for C$_{16}$H$_{12}$ClNO$_4$ (M+H) calculated: 318.05; found: 318.00.

5h: TLC Rf=0.77 in EtOAc/Hex (1/1). Yield: 93%. $^1$H NMR (CDCl$_3$, 400 MHz): δ 8.05 (d, J=7.6 Hz, 1H), 7.48 (t, J=8.0 Hz, 1H), 7.27 (t, J=8.0 Hz, 1H), 7.25 (d, J=7.6 Hz, 1H), 6.26 (br s, 2H), 3.49 (br s, 2H), 3.39 (br s, 2H), 2.59 (s, 3H), 1.82 (d, J=8.8 Hz, 1H), 1.56 (d, J=8.8, 1H); $^{13}$C NMR (CDCl$_3$, 75 MHz): δ 169.9, 136.2, 134.8, 133.3, 132.4, 130.7, 127.76, 125.8, 51.4, 44.9, 43.3, 21.3. MS for C$_{17}$H$_{15}$NO$_4$ (M+H) calculated: 298.10; found: 298.00.

5i: TLC Rf=0.49 in EtOAc/Hex (1/1). Yield: 97%. $^1$H NMR (CDCl$_3$, 400 MHz): δ 7.38 (d, J=8.4 Hz, 2H), 7.26 (t, J=8.4 Hz, 1H), 6.25 (br s, 2H), 3.50 (br s, 2H), 3.39 (br s, 2H), 1.81 (d, J=7.2 Hz, 1H), 1.57 (d, J=7.2, 1H); $^{13}$C NMR (CDCl$_3$, 75 MHz): δ 169.9, 134.8, 133.5, 129.6, 128.5, 127.8, 51.2, 44.4, 43.0; MS for C$_{16}$H$_{11}$Cl$_2$NO$_4$ (M+H) calculated: 351.02; found: 351.00.

$^1$H, $^{13}$C NMR and MS Assignment of Compounds 6a,d-f

6a: Yield: 60%. $^1$H NMR (D$_2$O, 400 MHz, pD=4.0, TFA salt, presaturated): 5.50 (d, J=4.0 Hz, H1'), 3.72-3.63 (m, H3', H4, H6), 3.46 (t, J=8.8 Hz, H4'), 3.40-3.32 (m, H5', H3, H6'), 3.24-3.19 (m, H5, H2'), 3.13 (td, J=10, 3.8 Hz, H1), 2.32 (td, J=8.8, 4.0 Hz, H2eq), 1.82 (s, —COCH$_3$), 1.67 (q, J=8.8 Hz, H2ax); $^{13}$C NMR (D$_2$O, 75 MHz): δ 169.6, 96.8 (C1'), 79.0 (C3'), 75.0 (C4'), 72.4 (C5'), 71.8 (C6), 70.2 (C5), 68.3 (C4), 54.0 (C2'), 49.8 (C1), 48.2 (C3), 39.2 (C6'), 28.8 (C2), 21.9 (—COCH3); MS (ES) for C$_{14}$H$_{28}$N$_4$O$_7$ (M+Na) calculated: 387.20; found: 387.20.

6d: Yield: 80%. $^1$H NMR (D$_2$O, 400 MHz, pD=4.0, TFA salt, presaturated): 7.59 (d, J=8.0 Hz, ArH2, ArH6), 7.45 (t, J=6.8 Hz, ArH4), 7.35 (t, J=8.0 Hz, ArH3 ArH5), 5.55 (d, J=4.0 Hz, H1'), 3.81-3.70 (m, H3', H6, H4), 3.62 (m, H6'), 3.49 (t, H4'), 3.40-3.30 (m, H5', H5, H3), 3.26 (br d, J=13.2 Hz, H2'), 3.13 (td, J=10.0, 4.0 Hz, H1), 2.32 (td, J=12.0, 4.0 Hz, H2eq), 1.67 (q, J=12 Hz, H2ax); $^{13}$C NMR (D$_2$O, 75 MHz) δ 167.7, 135.4, 132.2, 128.7, 126.5, 97.0 (C1'), 79.0 (C3'), 75.2 (C4'), 72.8 (C5'), 72.0 (C6), 71.0 (C5), 69.0 (C4), 54.0 (C2'), 50.0 (C1), 48.6 (C3), 40.0 (C6'), 28.5 (C2); MS (ESI) for C$_{19}$H$_{30}$N$_4$O$_7$ (M+Na) calculated: 439.21; found: 439.11.

6e: Yield: 75%. $^1$H NMR (D$_2$O, 400 MHz, presaturated): δ 7.24-7.14 (m, 5H), 5.48 (d, J=4.4, H1'), 3.73-3.65 (m, H3', H4, H6), 3.47 (s, 2H, CO—CH2-Ph), 3.45-3.40 (m, H6', H4'), 3.40-3.30 (m, H5', H6, H3), 3.17-3.07 (m, H5, H1, H2'), 2.32 (td, J=12.0, 4.0 Hz, H2eq), 1.67 (q, J=12.0 Hz, H2ax); $^{13}$C NMR (D$_2$O, 75 MHz) δ 169.8, 135.1, 131.8, 130.0, 127.6, 97.2 (C1'), 79.4 (C3'), 75.6 (C4'), 72.8 (C5'), 72.0 (C6), 70.2 (C5), 69.1 (C4), 54.0 (C2'), 50.0 (C1), 48.9 (C3), 42.6 (CH₂Ph), 38.0 (C6'), 28.4 (C2); MS (ESI) for C$_{20}$H$_{32}$N$_4$O$_7$ (M+H) calculated: 441.23; found: 441.20.

6f: Yield: 85%. ¹H NMR (D₂O, 400 MHz, presaturated): δ 7.84 (t, J=8.4 Hz, H5", H8"), 7.79 (d, J=8.0 Hz, H2"), 7.47 (m, H6", H7"), 7.40 (t, J=8.0 Hz, H3"), 7.36 (d, J=8.0 Hz, H4"), 5.33 (d, J=4.0 Hz, H1'), 3.98 (s, CO—CH2-Ar), 3.64-3.58 (m, H3', H4, H6), 3.48-3.35 (m, H4', H6', H5'), 3.32 (m, H3), 3.15 (dt, J=11.0, 4.0 Hz, H1), 2.88 (t, J=9.6 Hz, H5), 2.69 (dd, J=11.2, 4.0 Hz, H2'), 2.33 (td, J=12.4, 4.8 Hz, H2eq), 1.67 (q, J=12.8 Hz, H2ax); MS (ESI) for C$_{24}$H$_{34}$N$_4$O$_7$ (M+Na) calculated: 513.24; found: 513.20; ¹³C NMR (D₂O, 100 MHz, presaturated): δ 163.3 (CO), 133.8 (C10"), 131.8 (C9"), 131.1 (C1"), 129.1 (C4"), 128.9 (C2"), 128.5 (C8"), 126.9 (C3"), 126.4 (C6"), 126.2 (C5"), 123.7 (C7"), 96.7 (C1'), 79.0 (C3'), 75.2 (C4'), 72.7 (C5'), 71.9 (C6), 70.0 (C5), 68.6 (C4), 53.9 (C2'), 49.9 (C1), 48.7 (C3), 40.5 (CH2), 38.9 (C6'), 28.6 (C2).

¹H NMR and ¹³C NMR Assignment of Kanamycin A Sulfate

The ¹H NMR spectrum of kanamycin A free base (pD=10) was reported before. The ¹H and ¹³C NMR spectra of its sulfate salt (pD=4) are reported herein below. ¹H NMR (D₂O, 500 MHz, presaturated): δ 5.35 (d, J=3.5 Hz, H1'), 4.89 (d, J=3.5 Hz, H1"), 3.81 (dt, J=9.5, 3.5 Hz, H5"), 3.74 (dt, J=9.5, 3.5 Hz, H5'), 3.60 (br s, H6"), 3.57-3.54 (m, H3', H5), 3.51 (dd, J=10.5, 3.5 Hz, H2'), 3.43 (dd, J=10.5, 3.5 Hz, H2"), 3.35-3.29 (m, H4, H4"), 3.26 (t, J=9.5 Hz, H4'), 3.20 (m, H4), 3.16 (m, H6'), 3.03 (t, J=10.5 Hz, H3"), 3.02-2.89 (m, H1, H3, H6'), 1.95 (br d, J=12.5

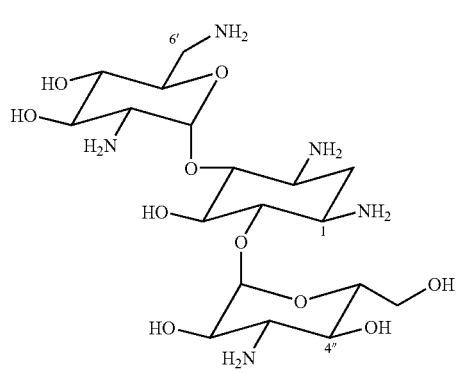

Hz, H2eq), 1.27 (q, J=12.5 Hz, H2ax); ¹³C NMR (D₂O, 125 MHz, by HSQC): δ 100.5 (C1"), 97.5 (C1'), 86.4 (C5'), 82.8 (C5"), 73.6 (C5), 72.3 (C2"), 72.0 (C4'), 71.3 (C4), 71.0 (C3'), 70.2 (C4"), 69.0 (C2'), 67.4 (C6), 60.0 (C6"), 54.6 (C3"), 50.5 (C1), 48.7 (C3), 40.8 (C6'), 33.1 (C2).

¹H NMR and ¹³C NMR Assignment of Ribostamycin A Sulfate

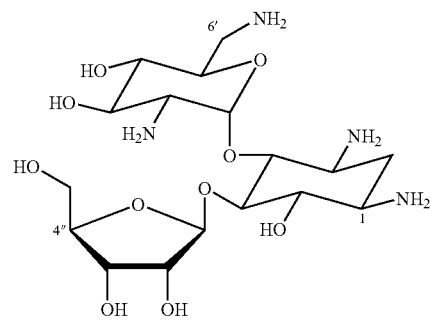

¹H NMR (D₂O, 500 MHz, pD=4, presaturated): δ 5.80 (d, J=4.0 Hz, H1'), 5.19 (br s, H1"), 4.06 (br d, H2"), 4.01 (t, J=7.0 Hz, H3"), 3.86 (m, H4", H5'), 3.81 (t, J=10.0 Hz, H4'), 3.74 (dd, J=12.5, 2.0 Hz, H5"), 3.68 (m, H6, H5), 3.52 (dd, J=12.5, 5.5 Hz, H5"), 3.47 (t, J=7.5 Hz, H4), 3.30 (dd, J=12.5, 3.0 Hz, H6'), 3.25 (t, J=10.0 Hz, H3'), 3.21 (dd, J=10.0, 4.0 Hz, H2'), 3.15-3.03 (m, H1, H3, H6'), 2.15 (td, J=12.5, 4.0 Hz, H2eq), 1.56 (q, J=12.5 Hz, H2ax); ¹³C NMR (D₂O, 125 MHz, by HSQC): δ 110.8 (C1"), 95.3 (C1'), 85.7 (C4), 82.8 (C4"), 78.3 (C5'), 75.8 (C2"), 73.7 (C6), 71.8 (C3'), 69.2 (C3"), 69.0 (C4'), 68.8 (C5), 61.4 (C5"), 54.6 (C2'), 50.7 (C1), 49.1 (C3), 41.1 (C6'), 30.8 (C2).

¹H, ¹³C NMR and HRMS Assignment of Compounds 9a-d

9a: TLC Rf=0.47 in EtOAc/Hex (1/1). Yield: 99%; the crude product was recrystallized using hexane to give earth-red crystals, m.p. 90-92° C. ¹H NMR (CDCl₃, 400 MHz): δ 6.20 (br s, 2H), 4.04 (s, 2H), 3.46 (br s, 2H), 3.34 (br s, 2H), 1.80 (d, J=8.8 Hz, 1H), 1.54 (d, J=8.8 Hz, 1H). ¹³C NMR (CDCl₃, 75 MHz) δ 169.5, 135.0, 51.6, 45.1, 43.7, 21.9. HRMS for C$_{11}$H$_{10}$NO$_4$ calculated: 298.98 (100) and 300.98 (97); found: 299.00 (100) and 301.00 (97).

9b: TLC Rf=0.60 in EtOAc/Hex (1/1). Yield: >99%; the crude product was recrystallized using hexane to give yellowish crystals, m.p. 118-120° C. ¹H NMR (CDCl₃, 400 MHz): δ 6.20 (br s, 2H), 3.58 (t, J=7.2 Hz, 2H), 3.46 (br s, 2H), 3.34 (br, s, 2H), 3.17 (t, J=7.2 Hz, 2H), 1.80 (d, J=8.8 Hz, 1H), 1.54 (d, J=8.8 Hz, 1H); ¹³C NMR (CDCl₃, 75 MHz) δ 169.8, 135.0, 51.6, 45.1, 43.6, 35.0, 24.0. HRMS for C$_{12}$H$_{12}$NO$_4$, calculated: 312.98 (100) and 314.98 (97); found: 313.00 (100) and 315.00 (97).

9c: TLC Rf=0.40 in EtOAc/Hex (1/2). Yield: 97%; the crude product was recrystallized using hexane to give white crystals, m.p. 65-66° C. ¹H NMR (CDCl₃, 400 MHz): δ 6.19 (br s, 2H), 3.49 (t, J=6.4 Hz, 2H), 3.45 (br s, 2H), 3.33 (br s, 2H), 2.76 (t, J=6.8 Hz, 2H), 2.25 (tt, J=6.8, 6.4 Hz, 2H), 1.79 (d, J=8.8 Hz, 1H), 1.54 (d, J=8.8 Hz, 1H); ¹³C NMR (CDCl₃, 75 MHz) δ 170.0, 135.0, 51.6, 45.0, 43.6, 31.9, 29.8, 27.8. HRMS for C$_{13}$H$_{14}$NO$_4$, calculated: 326.99 (100) and 328.99 (97); found 327.00 (100) and 329.00 (97).

9d: TLC Rf=0.36 in EtOAc/Hex (1/2). Yield: 95%; the crude product was recrystallized using hexane to give white crystals, m.p. 51-52° C. ¹H NMR (CDCl₃, 400 MHz): δ 6.18 (t, J=2.0 Hz, 2H), 3.44 (m, 4H), 3.30 (m, 2H), 2.57 (t, J=7.2 Hz, 2H), 2.05-1.83 (m, 4H), 1.78 (td, J=9.0, 2.0 Hz, 1H), 1.53 (d, J=9.0 Hz, 1H); ¹³C NMR (CDCl₃, 75 MHz) δ 170.1, 134.9, 51.6, 45.0, 43.5, 33.0, 31.7, 30.3, 23.5. HRMS for C$_{14}$H$_{16}$NO$_4$, calculated: 341.00 (100) and 343.00 (97); found: 341.01 (100) and 343.01 (97).

¹H, ¹³C NMR and HRMS Assignment of Compound 10a

Yield: 83%. ¹H NMR (D₂O, 500 MHz, presaturated): δ 8.48 (s, 1H), 8.26 (s, 1H), 6.05 (d, J=4.5 Hz, 1H), 5.57 (d, J=3.5 Hz, 1H), 4.44 (br s, 1H), 4.11 (m, 2H), 3.86 (s, 1H), 3.81 (t, J=9.2 Hz, 1H), 3.76-3.67 (m, 4H), 3.48-3.38 (m, 6H), 3.38-3.28 (m, 4H), 3.25-3.18 (m, 5H), 2.53 (t, J=6.5 Hz, 2H), 2.35 (m, 1H), 2.30 (t, J=6.0 Hz, 2H), 1.80 (q, J=12.5 Hz, 1H), 0.76 (s, 3H), 0.66 (s, 3H); $^{13}$C NMR (D$_2$O, 125 MHz, by HSQC and HMBC): δ 177.9, 174.9, 173.7, 150.2, 149.1, 144.8, 142.3, 118.7, 97.1, 88.0, 83.9, 79.8, 79.7, 75.8, 75.1, 74.0, 73.0, 72.8, 72.0, 71.9, 71.8, 69.6, 66.0, 54.0, 50.2, 48.9, 40.0, 38.7, 35.9, 35.8, 34.8, 31.6, 28.3, 21.2, 18.8; HRMS for C$_{35}$H$_{62}$N$_{11}$O$_{23}$P$_3$S (M+H), calculated: 1130.3034; found: 1130.3035.

$^{1}$H, $^{13}$C NMR and HRMS Assignment of Compound 11

Yield: 72%. $^{1}$H NMR (D$_2$O, 500 MHz, presaturated): δ 8.49 (s, 1H), 8.27 (s, 1H), 6.06 (d, J=4.5 Hz, 1H), 5.32 (d, J=4.5 Hz, 1H), 4.96 (d, J=3.5 Hz, 1H), 4.44 (br s, 1H), 4.10 (m, 2H), 3.86 (s, 1H), 3.78-3.61 (m, 9H), 3.58-3.52 (m, 3H), 3.46-3.40 (m, 4H), 3.36-3.28 (m, 5H), 3.18 (m, 2H), 3.14 (m, 4H), 2.53 (t, J=6.5 Hz, 2H), 2.40 (m, 1H), 2.30 (t, J=6.5 Hz, 2H), 1.74 (q, J=12.5 Hz, 1H), 0.77 (s, 3H), 0.66 (s, 3H); $^{13}$C NMR (D$_2$O, 125 MHz, by HSQC and HMBC): δ 174.8, 174.0, 173.2, 150.4, 149.5, 144.6, 142.0, 118.5, 100.8, 98.1, 87.5, 83.8, 83.6, 79.4, 74.4, 74.0, 73.6, 72.8, 72.2, 72.1, 72.0, 71.3, 71.2, 70.6, 68.0, 65.5, 65.3, 55.0, 50.0, 48.6, 46.7, 40.0, 39.9, 38.4, 38.3, 37.8, 37.7, 31.8, 28.4, 22.0, 20.0; HRMS for C$_{41}$H$_{72}$N$_{11}$O$_{28}$P$_3$S (M+H) calculated: 1291.6264; found: 1291.6267.

$^{1}$H, $^{13}$C NMR and HRMS Assignment of Compound 12

Yield: 67%. $^{1}$H NMR (D$_2$O, 400 MHz, presaturated): δ 8.51 (s, 1H), 8.29 (s, 1H), 6.09 (d, J=4.2, 1H), 5.74 (d, J=4.0, 1H), 5.20 (s, 1H), 4.46 (br s, 1H), 4.14 (m, 2H), 4.08 (d, J=6.0 Hz, 1H), 4.03 (t, J=7.2 Hz, 1H), 3.96 (t, J=9.6 Hz, 1H), 3.89 (s, 2H), 3.82-3.71 (m, 4H), 3.67 (dt, J=9.6, 4.0 Hz, 1H), 3.59 (t, J=9.2 Hz, 1H), 3.54-3.48 (m, 4H), 3.36 (m, 4H), 3.28-3.18 (m, 8H), 2.56 (t, J=6.5 Hz, 2H), 2.39 (m, 1H), 2.34 (t, J=6.0 Hz, 1H), 1.87 (q, J=12.0 Hz, 1H), 0.81 (s, 3H), 0.71 (s, 3H); $^{13}$C NMR (D$_2$O, 125 MHz, by HSQC and HMBC): δ 175.0, 174.0, 173.0, 151.0, 149.4, 142.8, 139.6, 118.6, 110.4, 96.8, 87.8, 84.3, 83.6, 82.2, 76.0, 75.6, 74.5, 74.0, 72.5, 72.0, 71.9, 71.5, 70.3, 69.0, 68.5, 65.2, 61.8, 54.0, 50.0, 49.0, 39.9, 39.6, 38.5, 35.8, 35.6, 34.7, 31.2, 28.5, 21.8, 18.6; HRMS for C$_{40}$H$_{70}$N$_{11}$O$_{28}$P$_3$S (M+H) calculated: 1261.3440; found: 1262.3455.

$^{1}$H, $^{13}$C NMR and HRMS Assignment of Compound 10b

Yield: 91%. $^{1}$H NMR (D$_2$O, 500 MHz, presaturated): δ 8.61 (s, 1H), 8.41 (s, 1H), 6.18 (d, J=5.0 Hz, 1H), 5.69 (d, J=4.5 Hz, 1H), 4.56 (br s, 1H), 4.24 (m, 2H), 3.97 (s, 1H), 3.91 (m, 1H), 3.87 (t, J=10.5 Hz, 1H), 3.82-3.80 (m, 2H), 3.60-3.57 (m, 4H), 3.53-3.29 (m, 1H), 2.76 (t, J=6.5 Hz, 2H), 2.62 (t, J=6.5 Hz, 2H), 2.53 (t, J=6.5 Hz, 2H), 2.48 (dt, J=12.0, 4.0 Hz, 1H), 2.42 (t, J=6.5 Hz, 2H), 1.80 (q, J=12.5 Hz, 1H), 0.89 (s, 3H), 0.78 (s, 3H); $^{13}$C NMR (D$_2$O, 125 MHz by HSQC and HMBC): δ 177.7, 175.0, 173.5, 150.0, 149.1, 145.1, 142.5, 119.2, 96.8, 88.7, 83.9, 79.2, 78.6, 75.6, 74.7, 74.0, 73.0, 72.8, 72.0, 71.9, 70.8, 69.0, 65.8, 54.2, 50.0, 49.1, 39.9, 38.8, 36.0, 35.9, 35.8, 30.9, 28.4, 27.6, 22.0, 19.7; HRMS for C$_{36}$H$_{64}$N$_{11}$O$_{23}$P$_3$S (M+H) calculated: 1144.3183; found: 1144.3188.

$^{1}$H, $^{13}$C NMR and HRMS Assignment of Compound 10c

Yield: 52%. $^{1}$H NMR (D$_2$O, 500 MHz, presaturated): δ 8.60 (s, 1H), 8.38 (s, 1H), 6.18 (d, J=5.5 Hz, 1H), 5.69 (d, J=4.0 Hz, 1H), 4.57 (br s, 1H), 4.34 (m, 2H), 3.97 (s, 1H), 3.93 (m, 1H), 3.87 (t, J=9.0 Hz, 1H), 3.84-3.77 (m, 2H), 3.61-3.55 (m, 5H), 3.52-3.43 (m, 4H), 3.38-3.28 (m, 6H), 2.59 (t, J=6.5 Hz, 2H), 2.49 (m, 3H), 2.42 (t, J=6.5 Hz, 2H), 2.33 (t, J=6.5 Hz, 2H), 1.92 (q, J=12.5 Hz, 1H), 1.79 (br t, J=7.0 Hz, 2H), 0.88 (s, 3H), 0.77 (s, 3H); $^{13}$C NMR (D$_2$O, 125 MHz, by HSQC and HMBC): δ 176.6, 174.8, 174.1, 151.0, 149.5, 146.0, 142.0, 118.0, 96.7, 87.8, 83.4, 79.2, 75.0, 74.4, 73.5, 72.5, 72.2, 71.7, 71.5, 70.6, 68.5, 65.0, 54.0, 49.2, 48.5, 38.9, 37.8, 36.8, 35.5, 35.3, 34.8, 30.5, 30.2, 28.0, 25.4, 20.8, 17.6; HRMS for C$_{37}$H$_{66}$N$_{11}$O$_{23}$P$_3$S (M+H) calculated: 1158.3346; found: 1158.3345.

$^{1}$H, $^{13}$C NMR and HRMS Assignment of Compound 10d

Yield: 93%. $^{1}$H NMR (D$_2$O, 500 MHz, presaturated): δ 8.61 (s, 1H), 8.40 (s, 1H), 6.18 (d, J=5.0 Hz, 1H), 5.69 (d, J=4.0, 1H), 4.56 (br s, 1H), 4.23 (m, 2H), 3.97 (s, 1H), 3.93 (br t, J=9.2 Hz, 1H), 3.87 (t, J=9.0 Hz, 1H), 3.81 (m, 2H), 3.61-3.55 (m, 5H), 3.52-3.43 (m, 4H), 3.38-3.28 (m, 6H), 2.59 (t, J=6.5 Hz, 2H), 2.50 (m, 3H), 2.42 (t, J=6.5 Hz, 2H), 2.25 (t, J=6.5 Hz, 2H), 1.90 (q, J=12.5 Hz, 1H), 1.50 (m, 2H), 1.51 (m, 2H), 0.88 (s, 3H), 0.77 (s, 3H); $^{13}$C NMR (D$_2$O, 125 MHz, by HSQC and HMBC): δ 178.0, 175.2, 173.6, 149.8, 148.8, 145.0, 142.4, 118.8, 97.0, 87.9, 83.6, 79.2, 75.0, 74.4, 73.5, 72.6, 72.3, 71.9, 71.6, 70.8, 68.8, 65.2, 53.8, 49.9, 48.4, 39.0, 38.8, 38.4, 35.5, 35.3, 35.0, 30.5, 30.2, 28.2, 27.8, 24.4, 21.0, 18.4; HRMS for C$_{38}$H$_{68}$N$_{11}$O$_{23}$P$_3$S (M+H) calculated: 1172.3496; found: 1172.3501.

Expression and Purification of AAC(6')-Ii

AAC(6')-Ii was obtained using a previously described protocol (Wright and Ladak, 1997). The *Escherichia coli* strain BL21 was transformed with a pET22b expression plasmid containing the AAC(6')-Ii gene. The bacteria were grown in Luria-Bertani (LB) media at 37° C. containing ampicillin (100 μg/mL). Expression of the protein was induced using isopropyl-β-D-thiogalactoside (IPTG). After harvesting the cells by centrifugation and washing them with a 0.85% NaCl solution, the cells were lysed by sonication. AAC(6')-Ii was purified in a two-step process: firstly, the lysate was ran through a Q-Sepharose ion exchange column (GE Healthsciences), and secondly the AAC(6')-Ii containing fractions were further purified using a Gentamicin agarose affinity column (BioRad).

AAC6'-Ii Inhibition Assay

Enzyme activity was monitored using a procedure described elsewhere (Williams and Northrop, 1978). Thus, reaction mixtures in HEPES (1 mM, pH=7.5) and containing 4,4'-dithiodipyridine (DTDP, 2 mM), aminoglycoside (200 μM), and AAC(6')-Ii (25 μg/mL) were prepared with varying concentrations of AcCoA. Reaction volumes were typically 400 μl. The assay mixtures were preincubated for 1 min at 37° C. The initial rates V were fit to Equation S1, where [S] is the concentration of AcCoA, Km is the Michaelis-Menten constant, and V$_m$ is the maximal velocity:

$$[S]/V=[S]/V_m+K_m/V_m \quad (S1)$$

The initial reaction velocity (steady-state) in the presence of inhibitors was measured as described above. The initial rates obtained at various concentrations of inhibitor were fit to Equation S2 for competitive inhibition, to Equation S3 for non-competitive inhibition, or to Equation S4 for uncompetitive inhibition, where [I] is the concentration of inhibitor and K$_i$ is the inhibition constant:

$$[S]/V=[S]/V_m+(1+[I]/K_i)K_m/V_m \quad (S2)$$

$$[S]/V=(1+[I]/K_i)[S]/V_m+K_m/V_m \quad (S3)$$

$$[S]/V=(1+[I]/K_i)[S]/V_m+(1+[I]/K_i)K_m/V_m \quad (S4)$$

It is to be understood that the invention is not limited in its application to the details of construction and parts as described hereinabove. The invention is capable of other embodiments and of being practiced in various ways. It is also understood that the phraseology or terminology used herein is for the purpose of description and not limitation. Hence, although the present invention has been described hereinabove by way of illustrative embodiments thereof, it can be modified, without departing from the spirit, scope and nature of the subject invention as defined in the appended claims.

REFERENCES

Agnelli et al., Chem. Int. Ed., 43:1562-1566, 2004.
Alper et al., Tet. Lett., 37:6029-6032, 1996.
Arya et al., Am. Chem. Soc., 123:5385-5395, 2001.
Arya et al., Bioorg. Med. Chem. Lett., 14:4643-4646, 2004.
Arya et al., J. Am. Chem. Soc. 125:10148-10149, 2003.
Arya et al., J. Am. Chem. Soc., 123:11093-11094, 2001.
Azucena and Mobashery, Drug Resistance Updates, 4:106-117, 2001.
Boehr et al., Biochemistry, 43:9846-9855, 2004.
Boto et al., J. Am. Chem. Soc., 105:1021-1028, 1983.
Burk et al., A. M Prot. Sci., 12:426-437, 2003.
Chou et al., Org. Lett., 6:585-588, 2004.
Coates et al., Nat. Rev., 1:895-910, 2002.
Culebras and Martinez, Front. Biosci., 4:D1-D8, 1999.
Ding et al., Chem. Int. Ed., 42:3409-3412, 2003.
Ding et al., Tet. Lett., 41:4049-4052, 2000.
Draker and Wright, Biochemistry, 43:446-454, 2004.
Draker et al., Biochemistry, 42:6565-6574, 2003.
Fourmy et al., J. Mol. Biol., 277:347-362, 1998.
Fourmy et al., Science, 274:1367-1375, 1997.
Gallego and Varani, Acc. Chem. Res., 34:836-843, 2001.
Georgiadis et al., Carb. Chem., 19:739-748, 1991.
Gerard et al., Antimicrobial Agents and Chemotherapy, 41:956-960, 1997.
Grapsas et al. J. Org. Chem., 59:1918-1922, 1994.
Greenberg et al., J. Am. Chem. Soc., 121:6527-6541, 1999.
Haddad et al., J. Am. Chem. Soc., 124:3229-3237, 2002.
Hanessian et al., Tet. Lett., 12:1035-1038, 1978.
Hanessian et al., Tetrahedron, 57:3255-3265, 2001.
Hanessian et al., Tetrahedron, 59:983-993, 2003.
Hermann, Chem. Int. Ed., 39:1890-1905, 2000.
Hermanson, In: Bioconjugate Techniques, Ch. 2., Academic Press, Inc, 1995.
Kim and Cole, J. Med. Chem., 44:2479-2485, 2001.
Li et al., Antimicrob. Chemother., 5:803-811, 2003.
Litovchick et al., Biochemistry, 39:2838-2852, 2000.
Liu et al., J. Am. Chem. Soc., 126:9196-9197, 2004.
Luedtke et al., Biochemistry, 39:11391-11403, 2003.
Magnet et al., Agents Chemother., 47:1577-1583, 2003.
Magnet et al., Biochemistry, 40:3700-3709, 2001.
Marmorstein Mol. Biol., 311:433-444, 2001.
Michael et al., Bioorg. Med. Chem. Lett., 7:1361-1371, 1999.
Moiseev et al., Russian J. Org. Chem., 39:1685-1701, 2003.
Murray, Clin. Microbiol. Rev., 3:46-65, 1990.
Nunns et al., Tet. Lett, 40:9341-9345, 1999.
Park et al., J. Am. Chem. Soc., 118:10150-10155, 1996.
Perrey et al., Tet. Lett., 42:1859-1861, 2001.
Poux et al., Proc. Nat. Acad. Sci. USA, 99:14065-14070, 2002.
Recht et al., EMBO J., 18:3133-3138, 1999.
Roestamadji and Mobashery, Bioorg. Med. Chem. Lett., 8:3483-3488, 1998.
Roestamadji et al., J. Am. Chem. Soc., 117:11060-11069, 1995.
Roestamadji et al., J. Am. Chem. Soc., 117:11060-11069, 1995.
Russell et al., Am. Chem. Soc., 124:3410-3411, 2003.
Ryu et al., Biochemistry, 41:10499-10509, 2002.
Sagar et al., Bioorg. Med. Chem., 12:3383-3390, 2004.
Sainlos et al., Eur. J. Org. Chem., 2764-2774, 2003.
Schepdael et al., Soc. Chim. Belg., Eur. Section, 101:709-718, 1992.
Seeberger et al., Synlett., 9:1323-1326, 2003.
Sucheck et al., Am. Chem. Soc., 122:5230-5231, 2000.
Tok and Bi, Curr. Topics Med. Chem., 3:1001-1019, 2003.
Tok et al., Tetrahedron, 55:5741-5748, 1999.
Vakulenko and Mobashery, Clin. Microbiol. Rev., 16:430-450, 2003.
Venot et al., Chem. Bio. Chem., 5:1228-1236, 2004.
Verhelst et al., Eur. J. Org. Chem., 2402-2410, 2004.
Vicens and Westhof, Biopolymers, 70:42-57, 2003.
Walsh, Nat. Rev. (Microbiology), 1:65-70, 2003.
Wang et al., Biochemistry, 36:768-779, 1997.
Wang, and Tor, J. Am. Chem. Soc., 119:8734-8735, 1997.
Williams and Northrop, J. Antibiotic, 32:1147-1154, 1979.
Williams et al., J. Biol. Chem., 253:5902-5907, 1978.
Wright and Ladak, Antimicrob. Agents Chemother., 41:956-960, 1997.
Wright et al., In: Resolving the Antibiotic Paradox, Rosen and Mobashery (Eds.), Kluwer Academic/Plenum Publishers, NY, 27-69, 1998.
Wright, Curr. Opin. Microbiol., 2:499-503, 1999.
Wybenga-Groot et al., Structure, 7:497-507, 1999.
Yang et al., J. Am. Chem. Soc., 113:3177-3178, 1991.
Yao et al., J. Bioorg. Med. Chem. Lett., 14:3733-3738, 2004.
Zheng and Cole, Bioorg. Chem., 31:398-411, 2003.

What is claimed is:

1. An inhibitor of aminoglycoside 6'-N-acetyltransferases of Formula I:

wherein:

R is selected from the group consisting of:

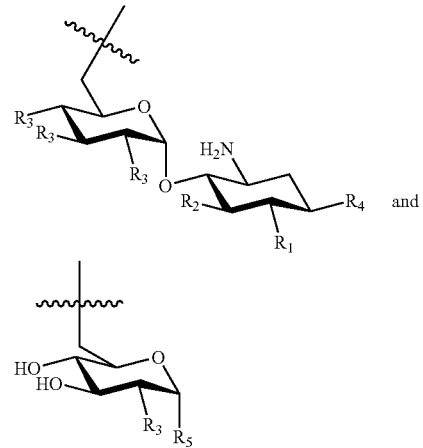

$R_1$ is selected from the group consisting of OH and

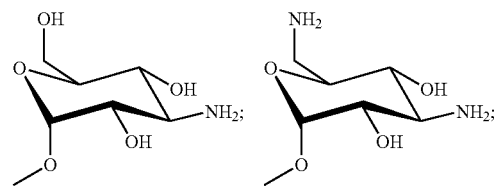

-continued

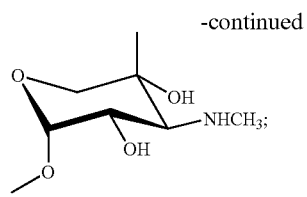

$R_2$ is selected from the group consisting of OH and

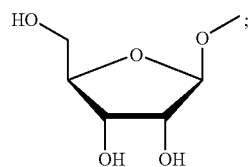

$R_3$ is selected from the group consisting of $NH_2$ and OH;
$R_4$ is selected from the group consisting of $NH_2$ and

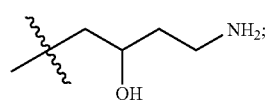

$R_5$ is selected from the group consisting of OMe, OEt OPr, and O-iPr;
X is selected from the group consisting of NH and O;
Y is selected from the group consisting of:

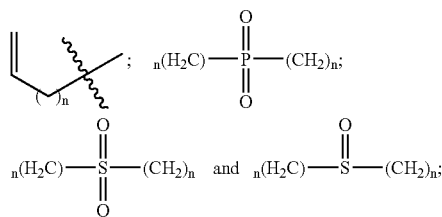

$R_6$ is selected from the group consisting of OH, $CH_3$, and $OCH_3$;
n is an integer ranging from 1 to 10; and
Z is selected from the group consisting of:

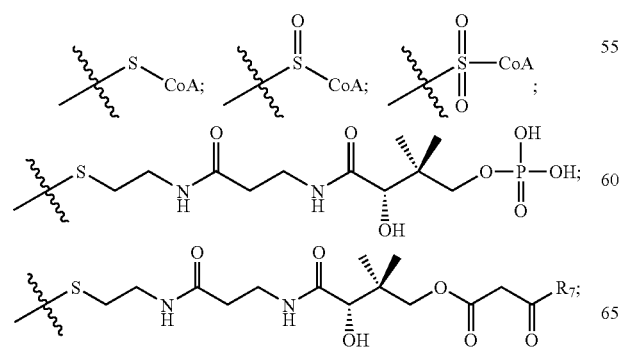

-continued

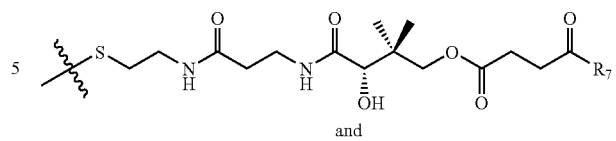

and

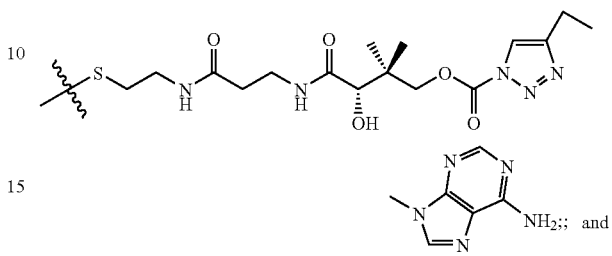

$R_7$ is selected from the group consisting of OH, OMe, OEt OPr, O-iPr, O-tBu and

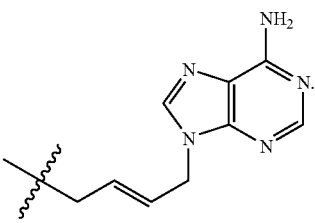

2. The inhibitor of claim 1, wherein:
R is

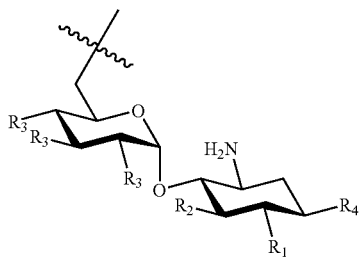

$R_1$ is selected from the group consisting of OH and

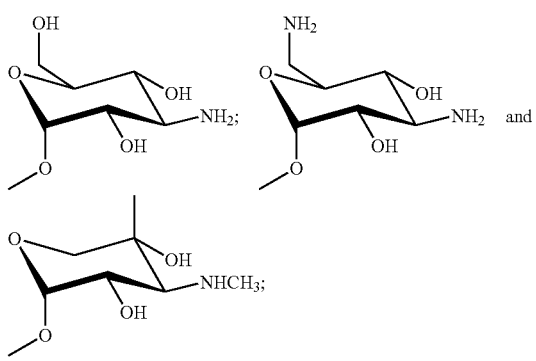

R₂ is selected from the group consisting of OH and

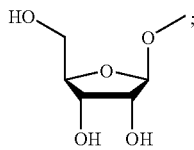

R₃ is selected from the group consisting of NH₂ and OH;
R₄ is selected from the group consisting of NH₂ and

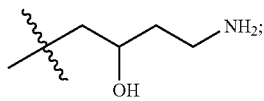

X is NH;
Y is

n is an integer ranging from 1 to 4; and
Z is

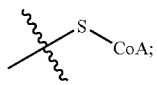

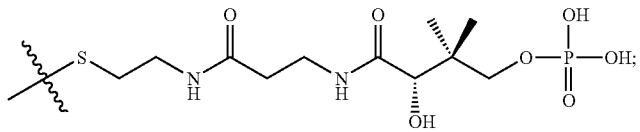

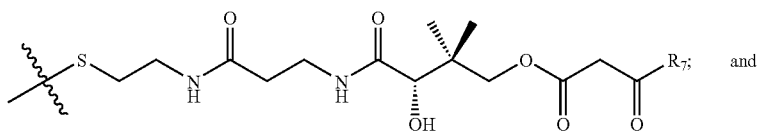

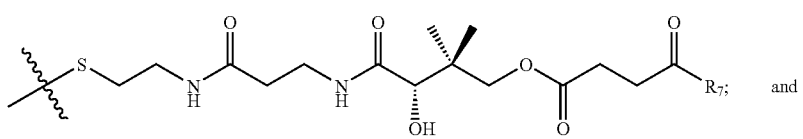

R₇ is selected from the group consisting of OH, OMe, OEt OPr, O-iPr, and O-tBu.

3. The inhibitor of claim 2, wherein:
R is

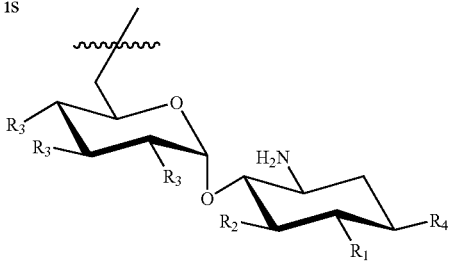

R₁ is OH;
R₂ is OH;
R₃ is selected from the group consisting of NH₂ and OH;
R₄ is NH₂;
X is NH;
Y is

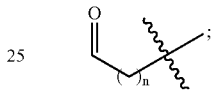

n is an integer ranging from 1 to 4; and
Z is

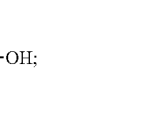

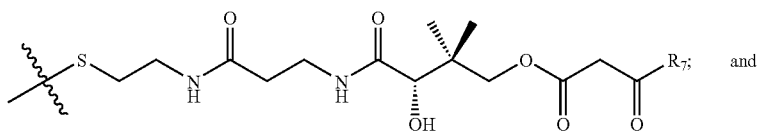

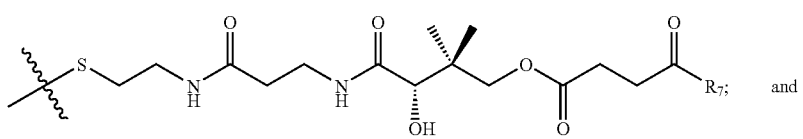

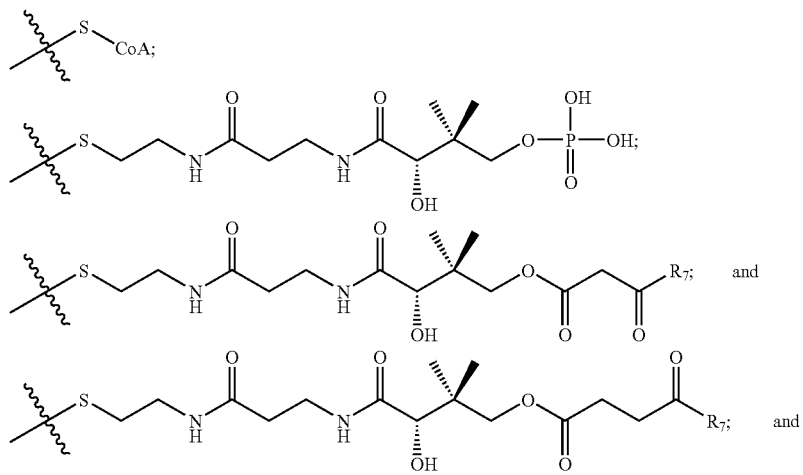

$R_7$ is selected from the group consisting of OH, OMe, OEt OPr, O-iPr and O-tBu.

4. The inhibitor of claim 1, wherein the aminoglycoside 6'-N-acetyltransferase is AAC(6')-Ii.

5. The inhibitor of claim 1, wherein the aminoglycoside 6'-N-acetyltransferase is AAC(6')-Iy.

6. An admixture comprising at least one inhibitor of aminoglycoside 6'-N-acetyltransferases as defined in claim 1 and one or more pharmaceutically acceptable carriers, excipients or diluents.

7. An admixture comprising at least one inhibitor of aminoglycoside 6'-N-acetyltransferases as defined in claim 1, and one or more antibacterial agents and one or more pharmaceutically acceptable carriers, excipients or diluents.

8. A pharmaceutical composition comprising at least one inhibitor of aminoglycoside 6'-N-acetyltransferase as defined in claim 1 and a pharmaceutically acceptable carrier, excipient, or diluent.

9. The inhibitor of claim 1, wherein Z is:

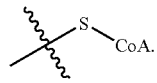

10. The inhibitor of claim 1, wherein Z is:

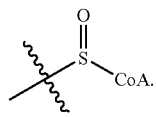

11. The inhibitor of claim 1, wherein Z is:

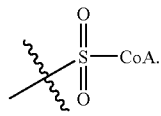

* * * * *

UNITED STATES PATENT AND TRADEMARK OFFICE
CERTIFICATE OF CORRECTION

PATENT NO. : 7,626,005 B2  Page 1 of 1
APPLICATION NO. : 11/359274
DATED : December 1, 2009
INVENTOR(S) : Karine Auclair et al.

It is certified that error appears in the above-identified patent and that said Letters Patent is hereby corrected as shown below:

In claim 1, column 43, line 32, after "OEt", insert a comma.

In claim 1, column 43, lines 36-45, delete chemical drawings and insert:

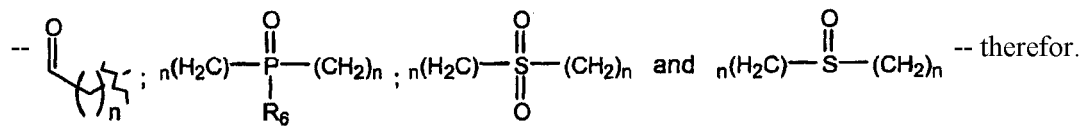 -- therefor.

In claim 1, column 44, lines 9-18, delete chemical drawing and insert:

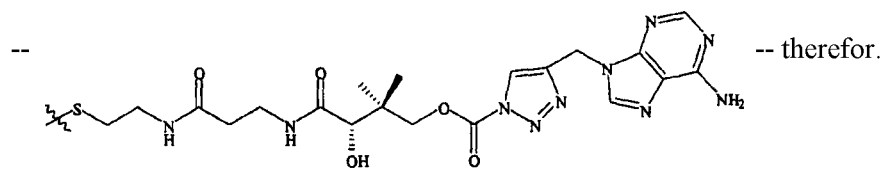 -- therefor.

In claim 1, column 44, line 20, after "OEt", insert comma.

Signed and Sealed this

Twenty-third Day of February, 2010

David J. Kappos
*Director of the United States Patent and Trademark Office*

UNITED STATES PATENT AND TRADEMARK OFFICE
CERTIFICATE OF CORRECTION

PATENT NO.         : 7,626,005 B2                                                    Page 1 of 1
APPLICATION NO.    : 11/359274
DATED              : December 1, 2009
INVENTOR(S)        : Auclair et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 383 days.

Signed and Sealed this

Ninth Day of November, 2010

David J. Kappos
*Director of the United States Patent and Trademark Office*